(12) United States Patent
Estera et al.

(10) Patent No.: US 10,932,803 B2
(45) Date of Patent: Mar. 2, 2021

(54) FEATURES FOR COMMUNICATION OF FLUID THROUGH SHAFT ASSEMBLY OF ULTRASONIC SURGICAL INSTRUMENT

(71) Applicant: Ethicon LLC, Guaynabo, PR (US)

(72) Inventors: Frederick L. Estera, Cincinnati, OH (US); Christopher Coyne, Paxton, MA (US); Joël Fontannaz, Bulle (CH); Lukas Glutz, Bern (CH); Amir Feriani, Auvernier (CH); Emmanuel Gremion, Echarlens (CH); Mathew D. Clopp, Santa Clara, CA (US)

(73) Assignee: Ethicon LLC, Guaynabo, PR (US)

(*) Notice: Subject to any disclaimer, the term of this patent is extended or adjusted under 35 U.S.C. 154(b) by 130 days.

(21) Appl. No.: 16/207,377

(22) Filed: Dec. 3, 2018

(65) Prior Publication Data
US 2019/0167295 A1 Jun. 6, 2019

Related U.S. Application Data

(63) Continuation of application No. 14/553,142, filed on Nov. 25, 2014, now Pat. No. 10,206,705.

(51) Int. Cl.
*A61B 17/32* (2006.01)
*A61B 17/26* (2006.01)
*A61B 17/29* (2006.01)

(52) U.S. Cl.
CPC ...... *A61B 17/26* (2013.01); *A61B 17/320092* (2013.01); *A61B 2017/2929* (2013.01);
(Continued)

(58) Field of Classification Search
CPC .. A61B 17/320092; A61B 2018/00011; A61B 2017/320084
See application file for complete search history.

(56) References Cited

U.S. PATENT DOCUMENTS

| 4,063,557 A | 12/1977 | Wuchinich et al. |
| 5,162,044 A | 11/1992 | Gahn et al. |

(Continued)

FOREIGN PATENT DOCUMENTS

| CN | 103747753 | 4/2014 |
| CN | 103945784 | 7/2014 |

(Continued)

OTHER PUBLICATIONS

Chinese Search Report dated Apr. 19, 2019 for Application No. 20158000940.8, 2 pages.
(Continued)

*Primary Examiner* — Anh T Dang
(74) *Attorney, Agent, or Firm* — Frost Brown Todd LLC

(57) ABSTRACT

A surgical apparatus comprises a body, a shaft assembly, a rotation input assembly, and an end effector. The shaft assembly defines a longitudinal axis and a first fluid passageway. The rotation input assembly is operable to rotate the shaft assembly about the longitudinal axis. The rotation input assembly defines a second fluid passageway. The second fluid passageway is in fluid communication with the first fluid passageway. The end effector is located at a distal end of the shaft assembly. The end effector comprises an ultrasonic blade. The end effector is in fluid communication with the first fluid passageway such that the end effector is configured to receive fluid communicated through the first and second fluid passageways.

20 Claims, 30 Drawing Sheets

(52) U.S. Cl.
CPC ............. *A61B 2017/320084* (2013.01); *A61B 2017/320094* (2017.08); *A61B 2017/320095* (2017.08); *A61B 2217/007* (2013.01)

(56) References Cited

U.S. PATENT DOCUMENTS

| | | | |
|---|---|---|---|
| 5,322,055 | A | 6/1994 | Davison et al. |
| 5,324,299 | A | 6/1994 | Davison et al. |
| 5,453,087 | A | 9/1995 | Malinowski |
| 5,873,873 | A | 2/1999 | Smith et al. |
| 5,980,510 | A | 11/1999 | Tsonton et al. |
| 6,056,735 | A | 5/2000 | Okada et al. |
| 6,193,709 | B1 | 2/2001 | Miyawaki et al. |
| 6,283,981 | B1 | 9/2001 | Beaupre |
| 6,309,400 | B2 | 10/2001 | Beaupre |
| 6,325,811 | B1 | 12/2001 | Messerly |
| 6,358,267 | B1 | 3/2002 | Murakami et al. |
| 6,423,082 | B1 | 7/2002 | Houser et al. |
| 6,669,690 | B1 | 12/2003 | Okada et al. |
| 6,773,444 | B2 | 8/2004 | Messerly |
| 6,783,524 | B2 | 8/2004 | Anderson et al. |
| 7,066,936 | B2 | 6/2006 | Ryan |
| 7,074,219 | B2 | 7/2006 | Levine et al. |
| 7,235,073 | B2 | 6/2007 | Levine et al. |
| 7,563,269 | B2 | 7/2009 | Hashiguchi |
| 8,057,498 | B2 | 11/2011 | Robertson |
| 8,328,834 | B2 | 12/2012 | Isaacs et al. |
| 8,348,880 | B2 | 1/2013 | Messerly et al. |
| 8,444,663 | B2 | 5/2013 | Houser et al. |
| 8,461,744 | B2 | 6/2013 | Wiener et al. |
| 8,591,459 | B2 | 11/2013 | Clymer et al. |
| 8,591,536 | B2 | 11/2013 | Robertson |
| 8,623,027 | B2 | 1/2014 | Price et al. |
| 8,652,132 | B2 | 2/2014 | Tsuchiya et al. |
| 8,662,745 | B2 | 3/2014 | Misuchenko et al. |
| 8,685,020 | B2 | 4/2014 | Weizman et al. |
| 8,911,460 | B2 | 12/2014 | Neurohr et al. |
| 8,974,447 | B2 | 3/2015 | Kimball et al. |
| 8,986,302 | B2 | 3/2015 | Aldridge et al. |
| 9,005,199 | B2 | 4/2015 | Beckman et al. |
| 9,023,071 | B2 | 5/2015 | Miller et al. |
| 9,113,943 | B2 | 8/2015 | Ross et al. |
| 9,993,260 | B2 | 6/2018 | Stokes et al. |
| 10,004,527 | B2 | 6/2018 | Gee et al. |
| 10,004,528 | B2 | 6/2018 | Faller et al. |
| 10,004,529 | B2 | 6/2018 | Stokes et al. |
| 10,034,685 | B2 | 7/2018 | Boudreaux et al. |
| 10,206,705 | B2 | 2/2019 | Estera et al. |
| 2006/0079874 | A1 | 4/2006 | Faller et al. |
| 2006/0265035 | A1 | 11/2006 | Yachi et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2009/0036914 | A1 | 2/2009 | Houser |
| 2010/0331873 | A1 | 12/2010 | Dannaher et al. |
| 2011/0152759 | A1* | 6/2011 | Clymer ............. A61B 5/14546 604/93.01 |
| 2012/0112687 | A1 | 5/2012 | Houser et al. |
| 2012/0116265 | A1 | 5/2012 | Houser et al. |
| 2012/0253371 | A1 | 10/2012 | Ross et al. |
| 2013/0090576 | A1 | 4/2013 | Stulen et al. |
| 2013/0303949 | A1 | 11/2013 | Kawaguchi et al. |
| 2014/0005668 | A1 | 1/2014 | Rhee et al. |
| 2014/0005701 | A1 | 1/2014 | Olson et al. |
| 2014/0012297 | A1 | 1/2014 | Ross et al. |
| 2014/0012298 | A1 | 1/2014 | Cunningham et al. |
| 2014/0012299 | A1 | 1/2014 | Stoddard et al. |
| 2014/0114334 | A1 | 4/2014 | Olson et al. |
| 2014/0135804 | A1 | 5/2014 | Weisenburgh et al. |
| 2014/0163549 | A1 | 6/2014 | Yates et al. |
| 2014/0180002 | A1 | 6/2014 | Voic |
| 2014/0330298 | A1 | 11/2014 | Arshonsky et al. |
| 2015/0080925 | A1 | 3/2015 | Schulte et al. |
| 2015/0148832 | A1 | 5/2015 | Boudreaux et al. |
| 2015/0148833 | A1 | 5/2015 | Stokes et al. |
| 2015/0148834 | A1 | 5/2015 | Gee et al. |
| 2015/0148835 | A1 | 5/2015 | Faller et al. |
| 2016/0143659 | A1 | 5/2016 | Glutz et al. |

FOREIGN PATENT DOCUMENTS

| | | |
|---|---|---|
| JP | 2014-000311 | 1/2014 |
| WO | WO 2012/116957 | 9/2012 |
| WO | WO 2013/183715 | 12/2013 |
| WO | WO 2013/062103 | 4/2015 |

OTHER PUBLICATIONS

Chinese first Office Action dated Apr. 28, 2019 for Application No. 201580063940.8, 5 pages.
European Examination Report dated Apr. 6, 2018 for Application No. 15813159.9, 4 pages.
International Search Report and Written Opinion dated Mar. 2, 2016 for International Application No. PCT/US2015/061557, 14 pages.
U.S. Appl. No. 61/410,603, filed Nov. 5, 2010.
U.S. Appl. No. 61/908,920, filed Nov. 26, 2013.

* cited by examiner

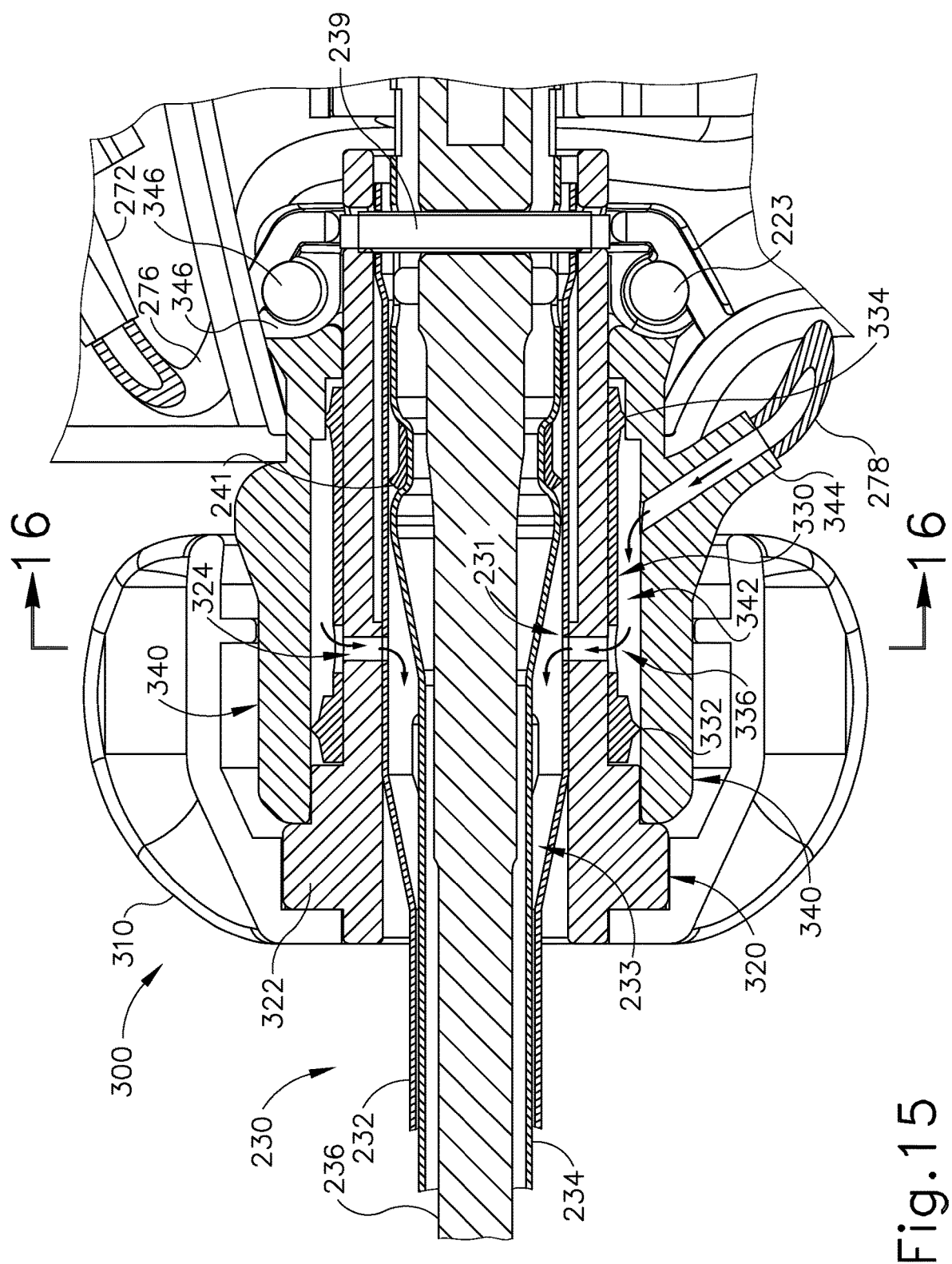

FEATURES FOR COMMUNICATION OF FLUID THROUGH SHAFT ASSEMBLY OF ULTRASONIC SURGICAL INSTRUMENT

This application is a continuation of U.S. patent application Ser. No. 14/533,142, entitled "Features for Communication of Fluid through Shaft Assembly of Ultrasonic Surgical Instrument," filed Nov. 25, 2014 and issued as U.S. Pat. No. 10,206,705 on Feb. 19, 2019.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014 the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 15 depicts a detailed cross-sectional side elevational view of the handle assembly of FIG. 6 and a shaft assembly of the instrument of FIG. 5, with fluid forced from the pump of FIG. 11 passing into an interior passageway of the shaft assembly;

Figure 1:
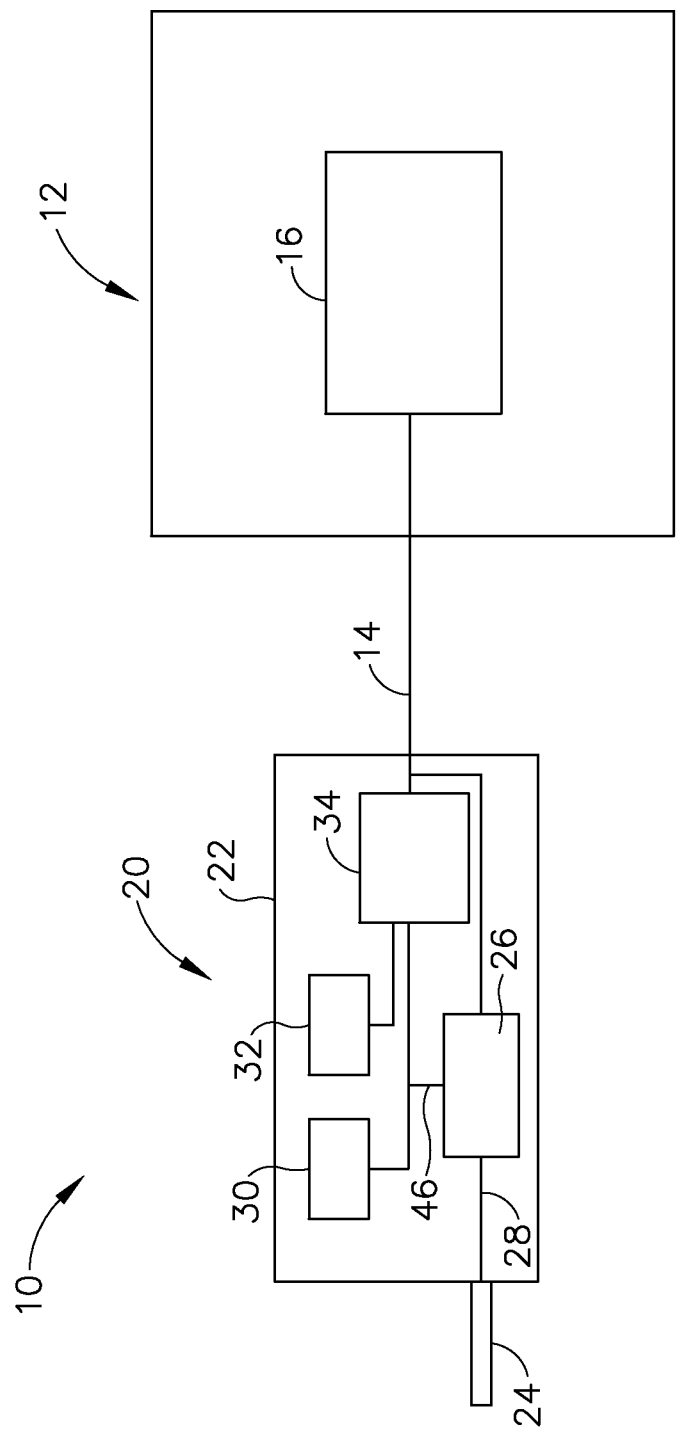
FIG. 1 depicts a block schematic view of an exemplary surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GENII, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,989,302 on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of an operator and manipulated by one hand (or two hands) of the operator during a surgical procedure. For instance, in some versions, handpiece (22) may be grasped like a pencil by the operator. In some other versions, handpiece (22) may include a scissor grip that may be grasped like scissors by the operator. In some other versions, handpiece (22) may include a pistol grip that may be grasped like a pistol by the operator. Of course, handpiece (22) may be configured to be gripped in any other suitable fashion. Furthermore, some versions of instrument (20) may substitute handpiece (22) with a body that is coupled to a robotic surgical system that is configured to operate instrument (20) (e.g., via remote control, etc.). In the present example, a blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handpiece (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths ($n\lambda/2$). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_0$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_0$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the operator via control selector (30), before the electrical power reaches ultrasonic transducer (26). Furthermore, generator (12) may be incorporated into handpiece (22) along with all other components of surgical system (10). For instance, one or more batteries (not shown) or other portable sources of power may be provided in handpiece (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations that may provided in instrument (20). It should be understood that the various examples of instrument (20) described below may be readily incorporated into surgical system (10) as described above. It should also be understood that the various components and operabilities of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
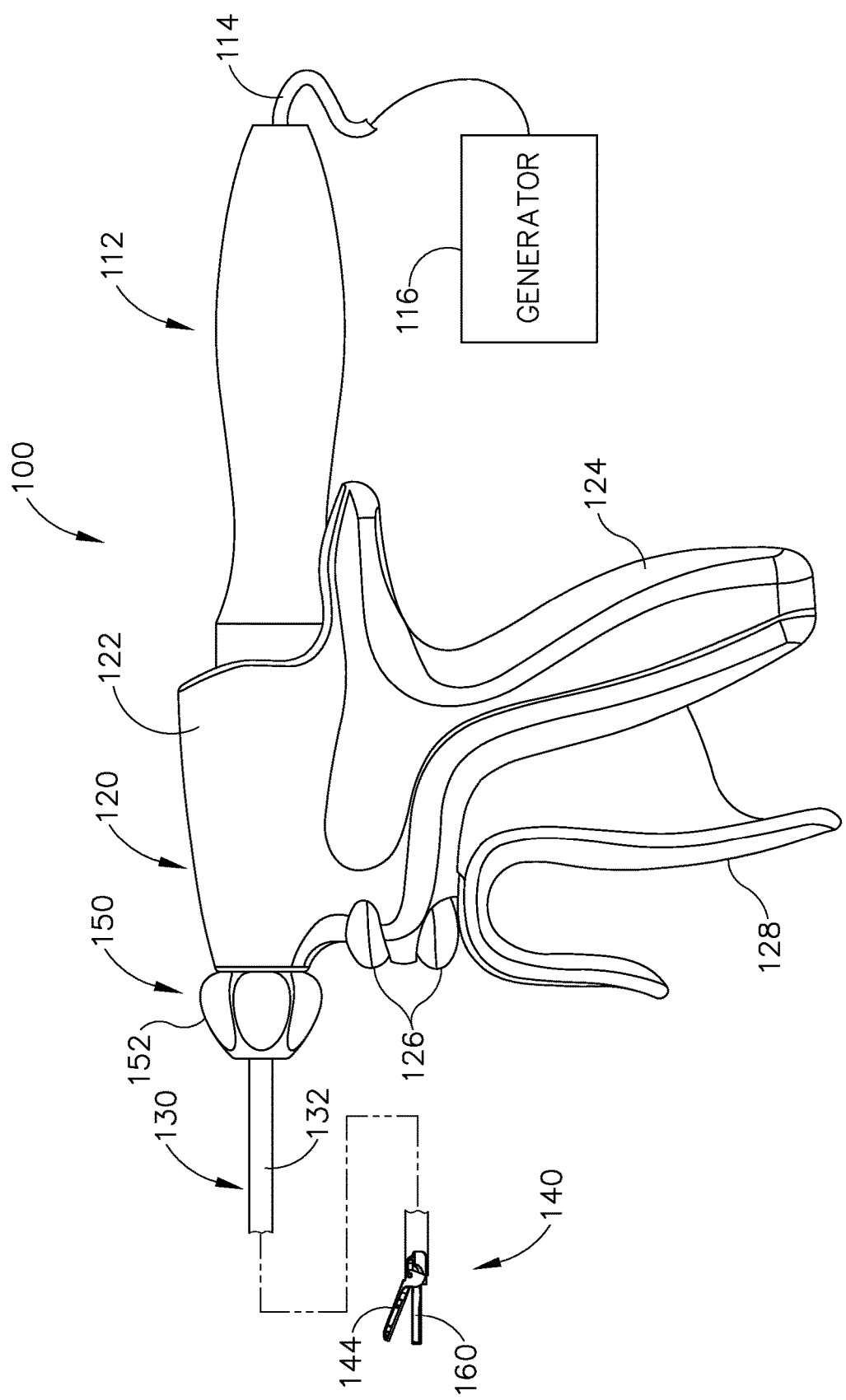
FIG. 2 depicts a side elevational view of an exemplary surgical instrument.

FIG. 2 illustrates an exemplary ultrasonic surgical instrument (100). At least part of instrument (100) may be constructed and operable in accordance with at least some of the teachings of U.S. Pat. Nos. 5,322,055; 5,873,873; 5,980,510; 6,325,811; 6,773,444; 6,783,524; 8,461,744; 8,623,027; U.S. Pub. No. 2006/0079874 now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; U.S. Pat. App. No. 61/410,603; and/or U.S. patent application Ser. No. 14/028,717, published as U.S. Pub. No. 2015/0080924 on Mar. 19, 2015. The disclosures of each of the foregoing patents, publications, and applications are incorporated by reference herein. As described therein and as will be described in greater detail below, instrument (100) is operable to cut tissue and seal or weld tissue (e.g., a blood vessel, etc.) substantially simultaneously. It should also be understood that instrument (100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (100) of the present example comprises a handle assembly (120), a shaft assembly (130), and an end effector (140). Handle assembly (120) comprises a body (122) including a pistol grip (124) and a pair of buttons (126). Handle assembly (120) also includes a trigger (128) that is pivotable toward and away from pistol grip (124). It should be understood, however, that various other suitable configurations may be used, including but not limited to a pencil-grip configuration or a scissor-grip configuration. End effector (140) includes an ultrasonic blade (160) and a pivoting clamp arm (144). Clamp arm (144) is coupled with trigger (128) such that clamp arm (144) is pivotable toward ultrasonic blade (160) in response to pivoting of trigger (128) toward pistol grip (124); and such that clamp arm (144) is pivotable away from ultrasonic blade (160) in response to pivoting of trigger (128) away from pistol grip (124). Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 4A.

An ultrasonic transducer assembly (112) extends proximally from body (122) of handle assembly (120). Transducer assembly (112) is coupled with a generator (116) via a cable (114). Transducer assembly (112) receives electrical power from generator (116) and converts that power into ultrasonic vibrations through piezoelectric principles. Generator (116) may include a power source and control module that is configured to provide a power profile to transducer assembly (112) that is particularly suited for the generation of ultrasonic vibrations through transducer assembly (112). By way of example only, generator (116) may comprise a GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Shaft assembly (130) of the present example comprises an outer sheath (132) and an inner tube (176). Inner tube (176) is slidably disposed within outer sheath (132). As will be discussed in more detail below inner tube (176) is operable to translate longitudinally within outer sheath (132) relative to outer sheath (132) to selectively pivot clamp arm (144) toward and away from blade (160). Shaft assembly (130) of the present example further includes a rotation knob (139). Rotation knob (139) is operable to rotate the entire shaft assembly (130) and end effector (140) relative to handle assembly (120) about a longitudinal axis of shaft assembly (130). In some versions, rotation knob (139) is operable to selectively lock the angular position of shaft assembly (130) and end effector (140) relative to handle assembly (120) about the longitudinal axis of shaft assembly (130). For instance, rotation knob (139) may be translatable between a first longitudinal position, in which shaft assembly (130) and end effector (140) are rotatable relative to handle assembly (120) about the longitudinal axis of shaft assembly (130); and a second longitudinal position, in which shaft assembly (130) and end effector (140) are not rotatable relative to handle assembly (120) about the longitudinal axis of shaft assembly (130). Of course, shaft assembly (130) may have a variety of other components, features, and operabilities, in addition to or in lieu of any of those noted above. By way of example only, at least part of shaft assembly (130) may be constructed in accordance with at least some of the teachings of U.S. patent application Ser. No. 14/257,245, entitled "Clamp Arm Features for Ultrasonic Surgical Instrument," filed Apr. 21, 2014, published as U.S. Pub. No. 2014/0330298 on Nov. 6, 2014, the disclosure of which is incorporated by reference herein. Other suitable configurations for shaft assembly (130) will be apparent to those of ordinary skill in the art in view of the teachings herein.

Figure 3:
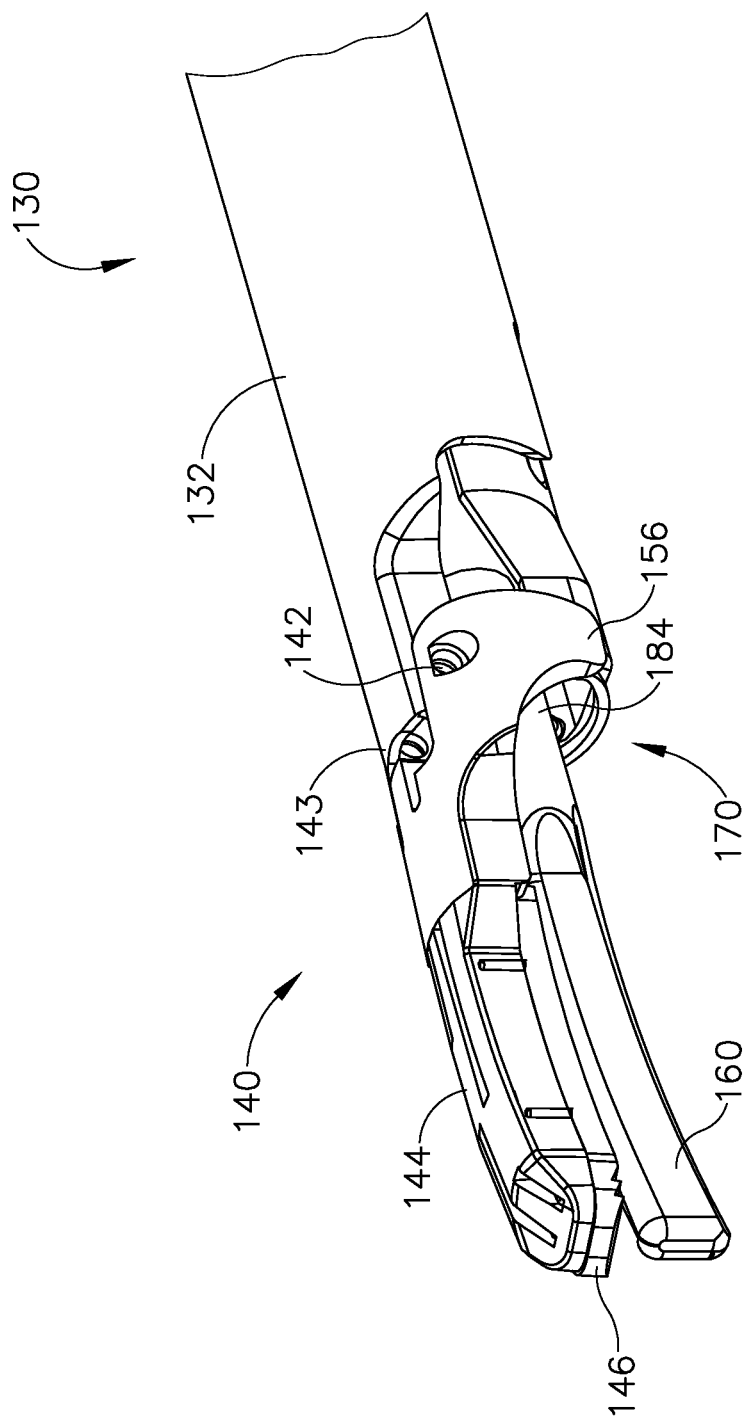
FIG. 3 depicts a perspective view of an end effector and a shaft assembly of the instrument of FIG. 2.

As best seen in FIG. 3, end effector (140) of the present example comprises clamp arm (144) and ultrasonic blade (160). Clamp arm (144) includes a primary clamp pad (146) and a secondary clamp pad (148) that are secured to the underside of clamp arm (144), facing blade (160). Clamp arm (144) is pivotably secured to a distally projecting tongue (143) of outer sheath (132) via a pin (142). Clamp arm (144) is operable to selectively pivot toward and away from blade (160) to selectively clamp tissue between clamp arm (144) and blade (160). A pair of arms (156) extend transversely from clamp arm (144) and are secured to a distal portion (170) of inner tube (176) that extends laterally between arms (156). Arms (156) are secured to distal portion (170) via a pair of integral, inwardly extending pins (151), which are rotatably disposed within a pair of through holes (not shown) of distal portion (170). Inner tube (176) is operable to translate longitudinally within outer sheath (132) relative to outer sheath (132) to selectively pivot clamp arm (144) toward and away from blade (160). In particular, inner tube (176) is coupled with trigger (128) such that clamp arm (144) pivots toward blade (160) in response to pivoting of trigger (128) toward pistol grip (124); and such that clamp arm (144) pivots away from blade (160) in response to pivoting of trigger (128) away from pistol grip (124). Clamp arm (144) may be biased toward the open position, such that (at least in some instances) the operator may effectively open clamp arm (144) by releasing a grip on trigger (128).

Figure 4A:
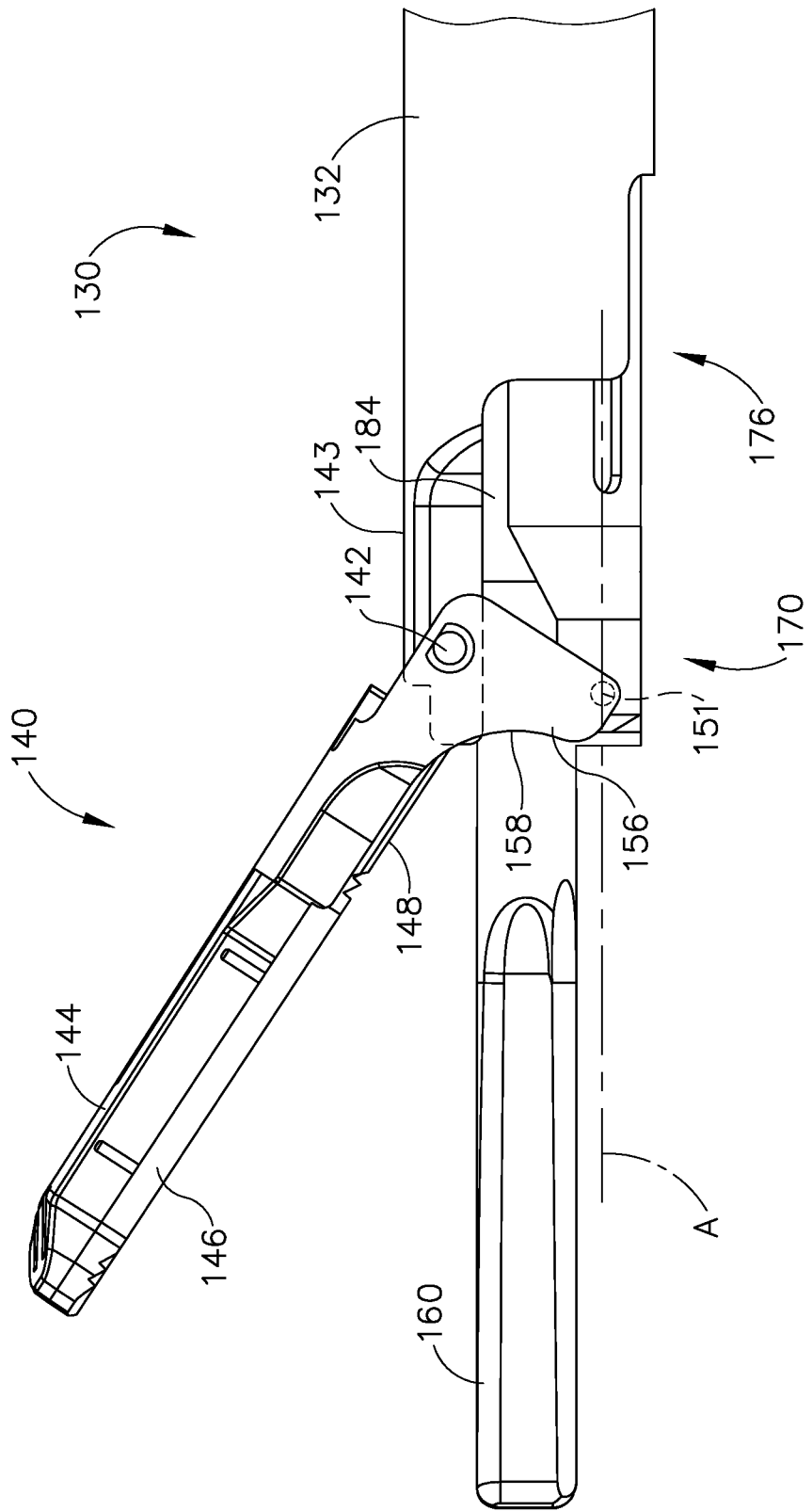
FIG. 4A depicts a side elevational view of the end effector of FIG. 3 with a clamp arm in an open position and with an inner tube in a distal position.
Figure 4B:
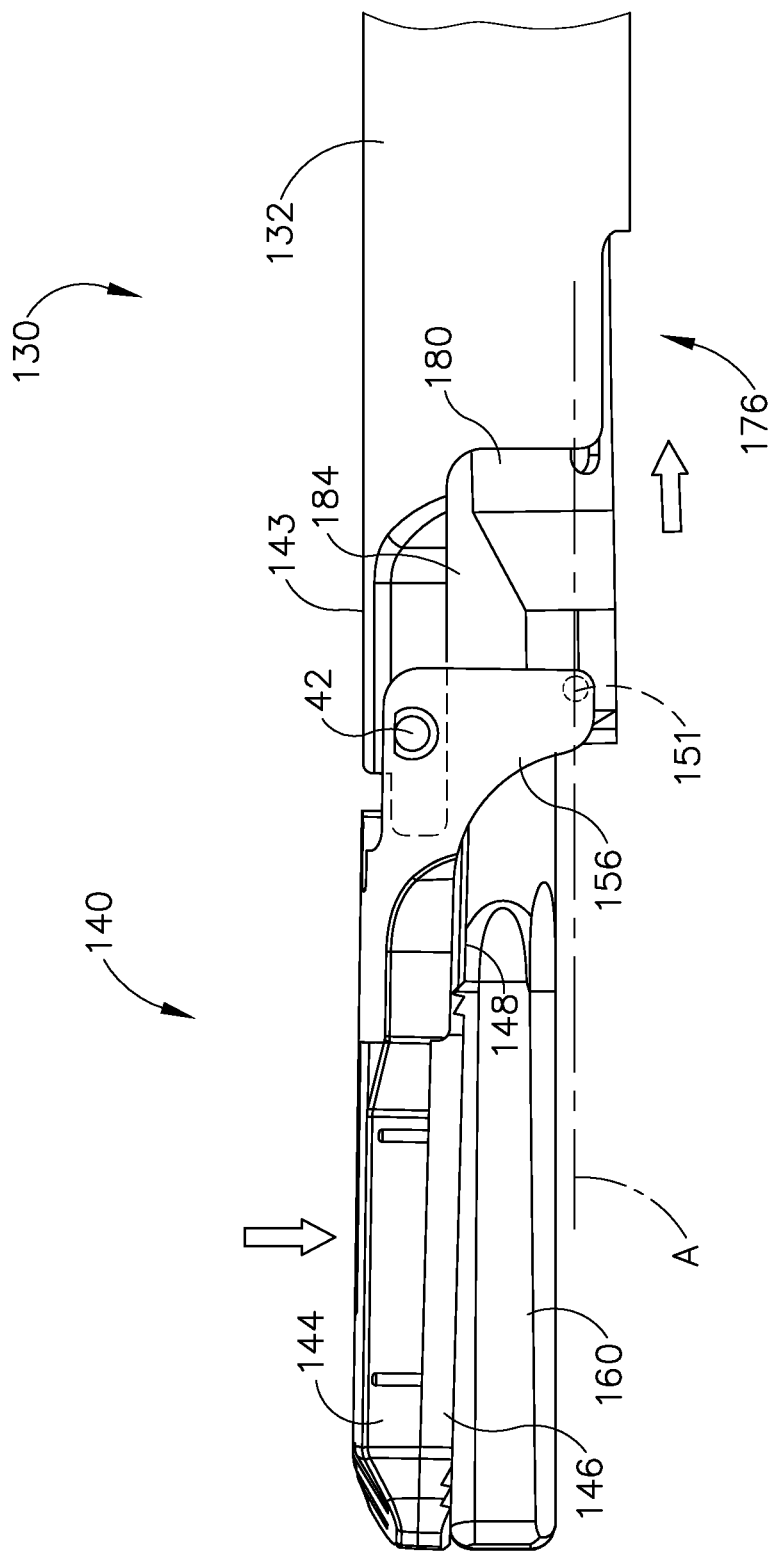
FIG. 4B depicts a side elevational view of the end effector of FIG. 3 with the clamp arm of FIG. 4A moved to a closed position by movement of the inner tube of FIG. 4A to a proximal position.
Figure 5:
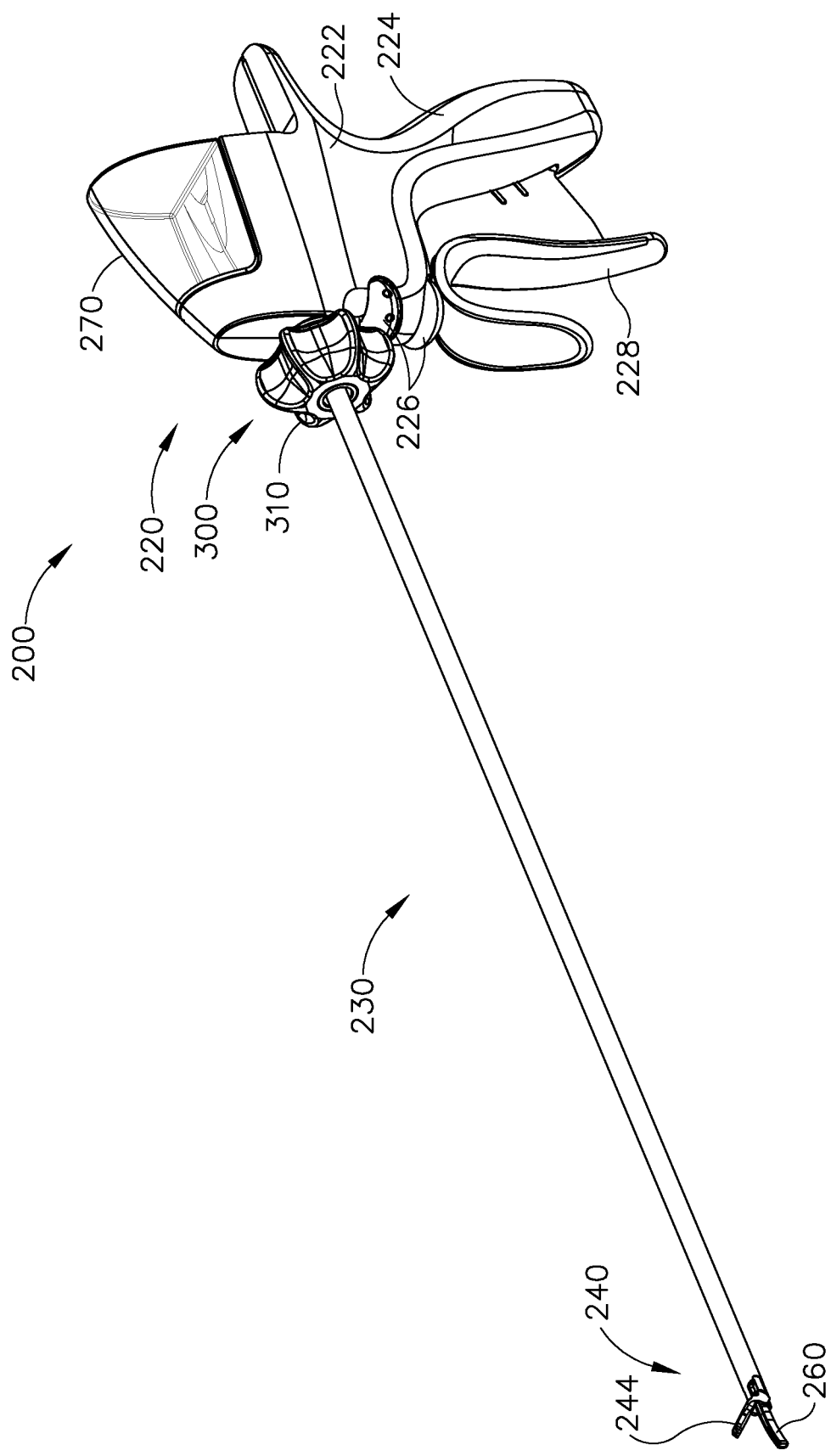
FIG. 5 depicts a perspective view of an exemplary alternative ultrasonic surgical instrument.

FIGS. 4A-4B show the operation of clamp arm (144) between an open position (FIG. 4A) and a closed position (FIG. 4B). As shown in FIG. 4A, when inner tube (176) is in a distal position relative to outer sheath (132), clamp arm (144) is in the open position. As shown in FIG. 4B, as inner tube (176) is moved proximally to a proximal position, clamp arm (144) is pivoted toward blade (160) to the closed position. It should be understood that clamp pad (146) may compress tissue against blade (160) as clamp arm (144) is moved toward the closed position.

Blade (160) of the present example is operable to vibrate at ultrasonic frequencies in order to effectively cut through and seal tissue, particularly when the tissue is being clamped between clamp pads (146, 148) and blade (160). Blade (160) is positioned at the distal end of an acoustic drivetrain. This acoustic drivetrain includes transducer assembly (112) and an acoustic waveguide (184). Transducer assembly (112) includes a set of piezoelectric discs (not shown) located proximal to a horn (not shown) of rigid acoustic waveguide (184). The piezoelectric discs are operable to convert electrical power into ultrasonic vibrations, which are then transmitted along acoustic waveguide (184) to blade (160) in accordance with known configurations and techniques. By way of example only, this portion of the acoustic drivetrain may be configured in accordance with various teachings of various references that are cited herein.

In the present example, the distal end of blade (160) is located at a position corresponding to an anti-node associated with resonant ultrasonic vibrations communicated through acoustic waveguide (184), in order to tune the acoustic assembly to a preferred resonant frequency $f_o$ when the acoustic assembly is not loaded by tissue. When transducer assembly (112) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through acoustic waveguide (184) to reach blade (160), thereby providing oscillation of blade (160) at the resonant ultrasonic frequency. Thus, when tissue is secured between blade (160) and clamp pads (146, 148), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (144) to also cauterize the tissue. While some configurations for an acoustic transmission assembly and transducer assembly (112) have been described, still other suitable configurations for an acoustic transmission assembly and transducer assembly (112) will be apparent to one or ordinary skill in the art in view of the teachings herein. Similarly, other suitable configurations for end effector (140) will be apparent to those of ordinary skill in the art in view of the teachings herein.

III. Exemplary Surgical Instrument with Liquid Cooled Ultrasonic Blade

In some instances, one or more regions of instrument (20, 100) may heat up during extended operation of instrument (20, 100) in a surgical procedure. By way of example only, blade (24, 160), clamp arm (144), and/or other portions of instrument (20, 100) may eventually heat up over time. Such heating may be caused by friction and/or other factors. To the extent that the heat is initially generated in one particular component of instrument (20, 100) (e.g., blade (24, 160) or clamp arm (144), etc.), such heat may be gradually transmitted to other portions of instrument (20, 100). It may be desirable to minimize such heating and/or otherwise manage such heating in order to avoid having heated portions of instrument (20, 100) contact tissue that should not be heated. For instance, the operator may wish for end effector (140) to be relatively cool when the operator wishes to use end effector (140) to perform spreading blunt dissections and/or simple tissue grasping, etc. It may also be desirable to minimize heat and/or otherwise manage heat in a way that does not significantly increase the size or operability of instrument (20, 100).

One merely exemplary way in which heat may be managed in instrument (20, 100) is to use a fluid to cool blade (24, 160). For instance, a cooling liquid (e.g., saline, etc.) may be applied to the proximal end of blade (24, 160). The cooling fluid may then be communicated distally along the rest of the length of blade (24, 160) to thereby cool blade (24, 160). The examples described below provide various structures and techniques through which a cooling liquid (or "liquid coolant") may be communicated to a blade such as blade (24, 160). While various examples of features configured to cool blade (24, 160) will be described in greater detail below, other examples will be apparent to those of ordinary skill in the art according to the teachings herein.

A. Overview of Exemplary Surgical Instrument with Liquid Cooled Ultrasonic Blade FIGS. 5-29 illustrate an exemplary ultrasonic surgical instrument (200) that is configured to operate substantially similar to instrument (100) discussed above except for the differences discussed below. It should therefore be understood that instrument (200) may include the same components and operabilities as instrument (20, 100), in addition to including the components and operabilities described below. Instrument (200) of the present example comprises a handle assembly (220), a shaft assembly (230), and an end effector (240). Handle assembly (220) comprises a body (222) including a pistol grip (224) and a pair of buttons (226). As with instrument (100) discussed above, body (222) of handle assembly (220) is configured to receive an ultrasonic transducer assembly (not shown). Handle assembly (220) also includes a trigger (228) that is pivotable toward and away from pistol grip (224). End effector (240) includes an ultrasonic blade (260) and a pivoting clamp arm (244). Clamp arm (244) is coupled with trigger (228) such that clamp arm (244) is pivotable toward ultrasonic blade (260) in response to pivoting of trigger (228) toward pistol grip (224); and such that clamp arm (244) is pivotable away from ultrasonic blade (260) in response to pivoting of trigger (228) away from pistol grip (224). In some versions, one or more resilient members are used to bias clamp arm (244) and/or trigger (228) to an open position.

Figure 7:
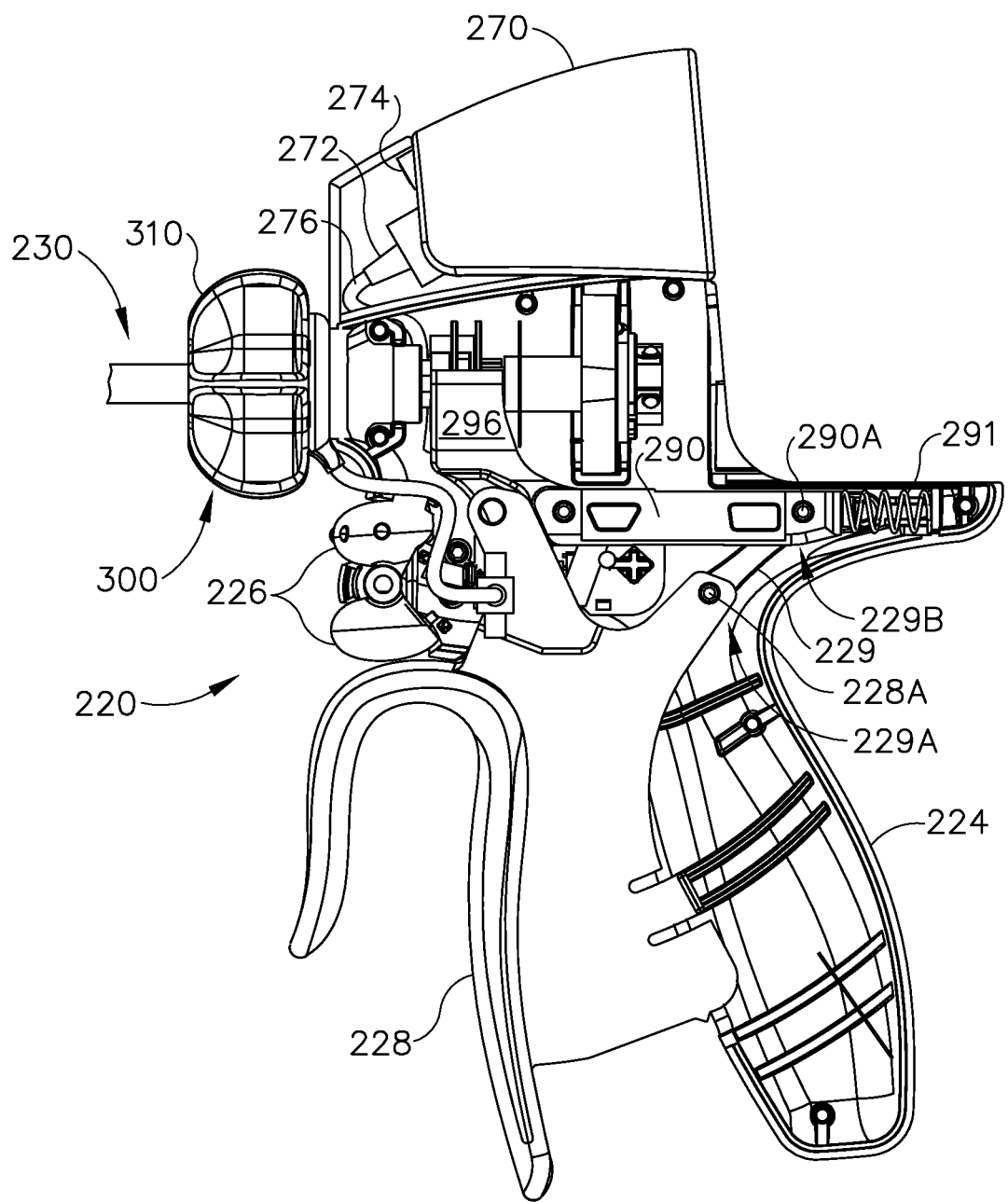
FIG. 7 depicts a side elevational view of the handle assembly of FIG. 6 with a housing shroud removed.
Figure 8:
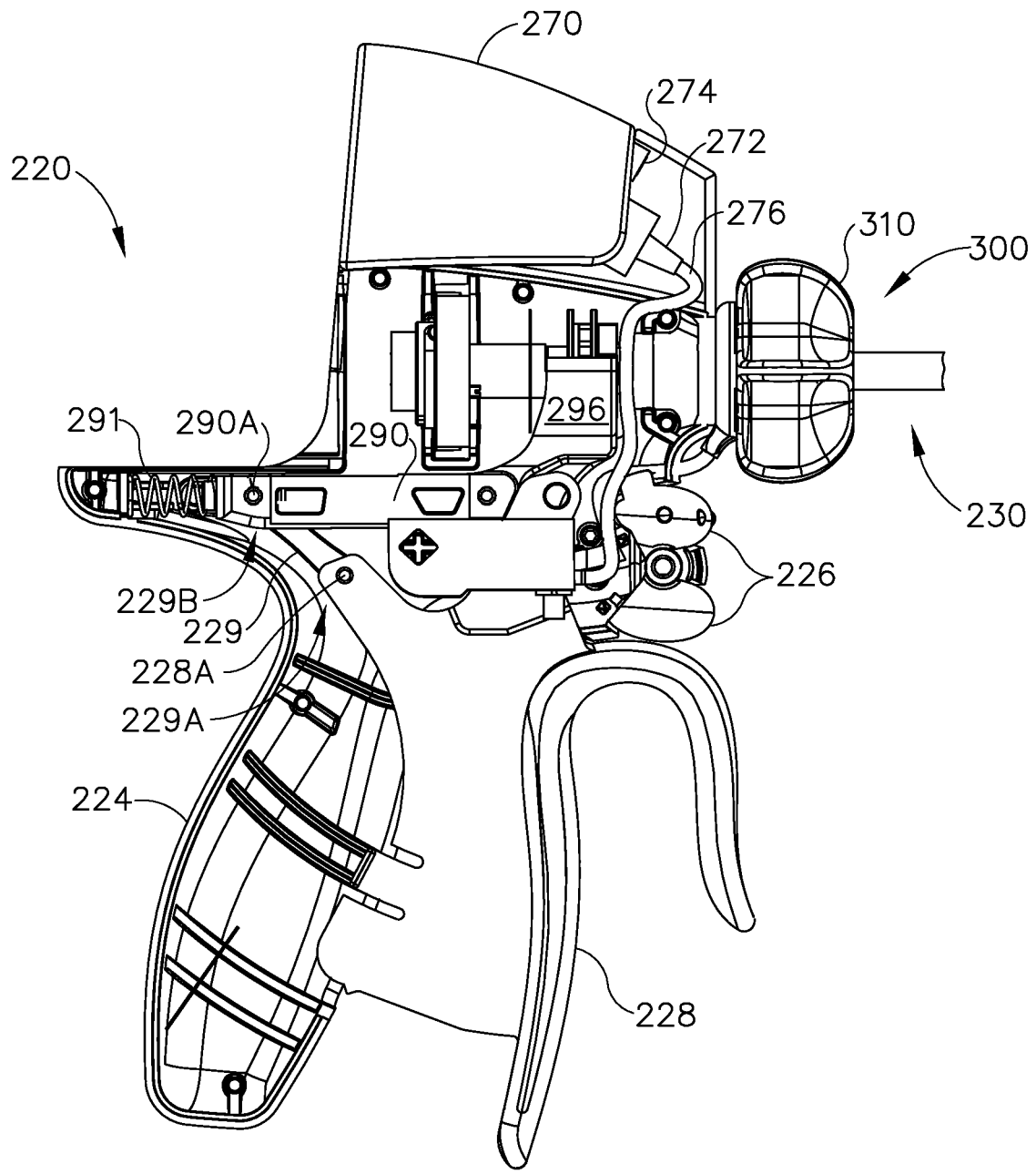
FIG. 8 depicts another side elevational view of the handle assembly of FIG. 6 with another housing shroud removed.
Figure 9:
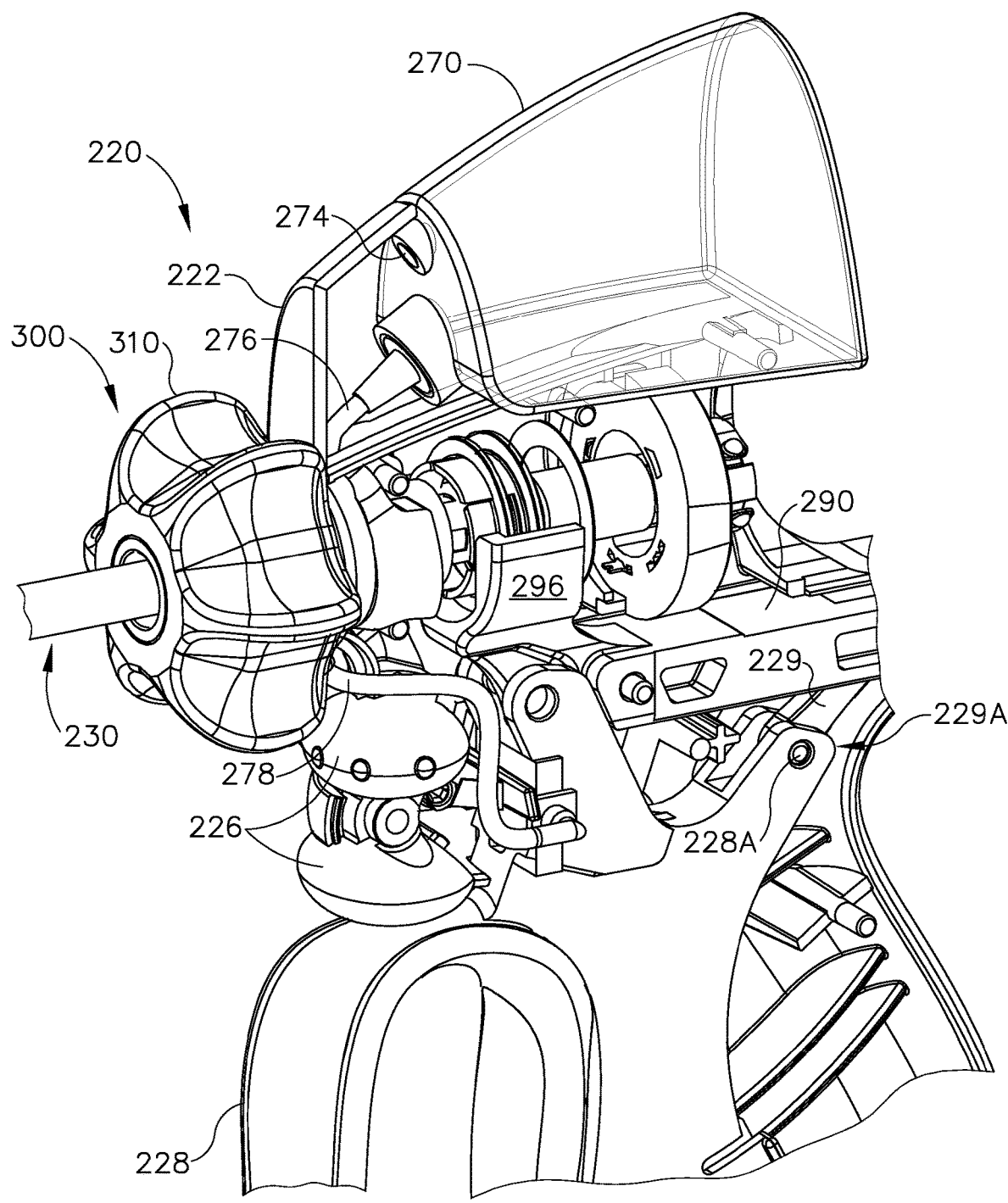
FIG. 9 depicts a detailed perspective view of the handle assembly of FIG. 6 with the housing shroud of FIG. 7 removed.
Figure 10:
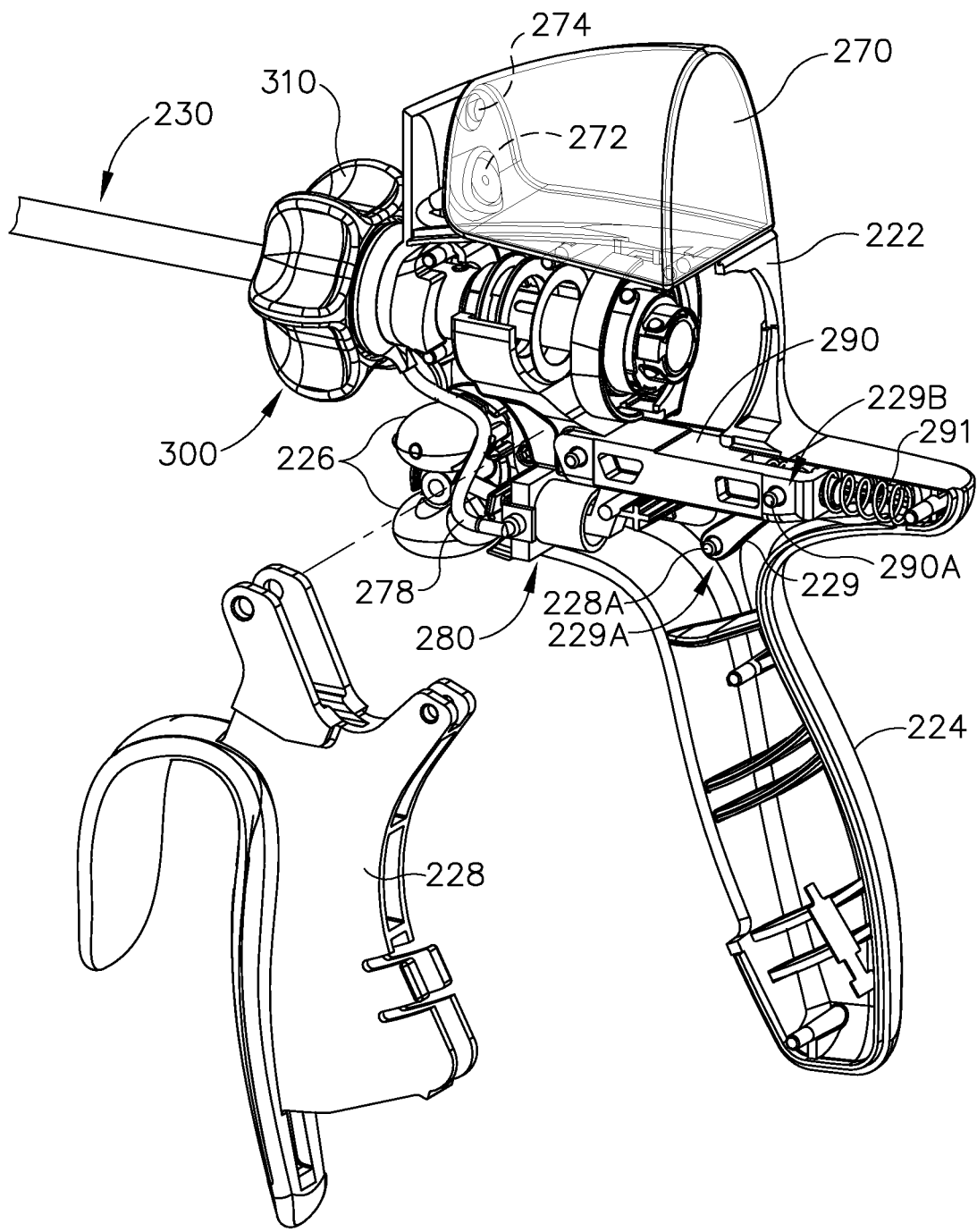
FIG. 10 depicts a perspective view of the handle assembly of FIG. 6 with the housing shroud of FIG. 7 removed and with a trigger of the handle assembly detached from the handle assembly.

Handle assembly (220) of the present example further comprises a fluid reservoir (270). Fluid reservoir (270) is configured to be filled with liquid coolant and to selectively retain the liquid coolant therein. By way of example only, fluid reservoir (270) may be configured to hold approximately 26 cubic centimeters of fluid. Alternatively, fluid reservoir (270) may have any other suitable capacity. Fluid reservoir (270) is configured to selectively couple with a top portion of body (222) of handle assembly (220). In some instances, fluid reservoir (270) may couple with body (222) in a snap-fit manner. Alternatively, fluid reservoir (270) may be coupled with body (222) in any other suitable manner as would be apparent to one of ordinary skill in the art. As best seen in FIGS. 6-10, fluid reservoir (270) comprises a valve (272) and a vent (274) formed in a distal portion of fluid reservoir (270). With fluid reservoir (270) coupled to body (222), valve (272) is configured to couple with a first tube (276), as best seen in FIGS. 7-9. While not shown, it should be understood that a fluidic connector and/or any other suitable kind of structure(s) may be used to couple valve (272) with first tube (276). In some versions, valve (272)

automatically opens to provide fluid communication between fluid reservoir (270) and first tube (276) as soon as fluid reservoir (270) is coupled with body (222). In some such versions, valve (272) automatically closes as soon as fluid reservoir (270) is decoupled from body. As will be discussed in more detail below, fluid reservoir (270) is configured to provide liquid coolant to a fluid pump (280) via first tube (276). As liquid coolant is communicated from fluid reservoir (270), vent (274) permits atmospheric air to flow into fluid reservoir (270) to thereby to prevent formation of a vacuum within fluid reservoir (270).

Figure 6:
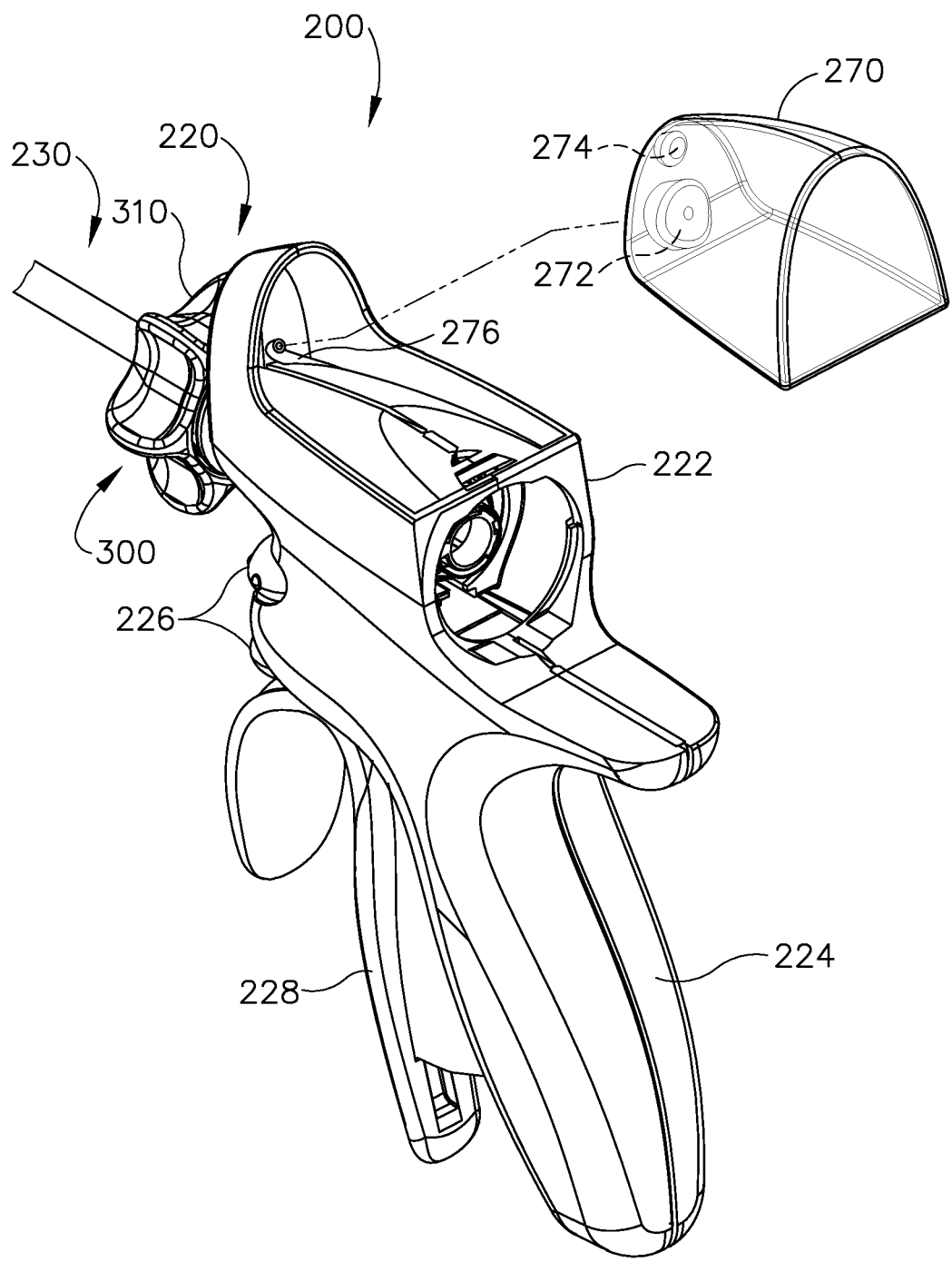
FIG. 6 depicts a perspective view of the handle assembly of the instrument of FIG. 5 with a fluid reservoir of the handle assembly detached from the handle assembly.

As shown in FIG. 6, fluid reservoir (270) may be detached from body (222) in order to refill fluid reservoir (270) with liquid coolant. A syringe (not shown) filled with liquid coolant may be coupled with valve (272) such that the liquid coolant may be passed into fluid reservoir (270) via valve (272). In some such versions, valve (272) includes a luer fitting to facilitate coupling with a conventional syringe. As fluid reservoir (270) is filled with liquid coolant, vent (274) permits air to flow out of fluid reservoir (270) to thereby prevent pressurization of the liquid coolant within fluid reservoir (270). In some alternative versions of fluid reservoir (270), it may be desirable to provide features that permit refilling of fluid reservoir (270) without fluid reservoir (270) having to be detached from body (222). Fluid reservoir (270) may comprise a self-sealing septum (not shown) that provides fluid access to the interior of fluid reservoir (270). The needle of a syringe filled with liquid coolant may pierce the septum such that the liquid coolant may be passed into fluid reservoir (270) through the septum. Fluid reservoir (270) may alternatively be configured and operable in accordance with at least some of the teachings of U.S. patent application Ser. No. 14/553,329, entitled "Features to Drive Fluid toward an Ultrasonic Blade of a Surgical Instrument," filed on Nov. 25, 2014, issued as U.S. Pat. No. 10,004,529 on Jun. 26, 2018, the disclosure of which is incorporated by reference herein. Other suitable ways in which reservoir (270) may be configured and filled will be apparent to those of ordinary skill in the art in view of the teachings herein. Similarly, other suitable ways in which reservoir (270) may be coupled with body (222) will be apparent to those of ordinary skill in the art in view of the teachings herein.

While reservoir (270) is integrated with body (222) in this example, it should be understood that reservoir (270) may be separate from body (222). For instance, reservoir (270) may comprise a conventional saline bag that is coupled with first tube (276) via a flexible conduit. As another merely illustrative alternative, reservoir (270) may be incorporated into ultrasonic generator (12) or some other piece of capital equipment. Other suitable locations for a source of liquid coolant will be apparent to those of ordinary skill in the art in view of the teachings herein.

FIGS. 7-10 and 14A-14C show interior components of handle assembly (220). Trigger (228) of handle assembly (220) is pivotably coupled to body (222) of handle assembly (220) such that trigger (228) is operable to pivot toward and away from pistol grip (224). Trigger (228) is coupled with a yoke (290) via a link (229) such that rotation of trigger (228) causes longitudinal translation of yoke (229). A first end (229A) of link (229) is rotatably coupled with a proximal portion of trigger (228) via a pin (228A). A second end (229B) of link (229) is rotatably coupled with a proximal portion of yoke (290) via a pin (290A). Yoke (290) is longitudinally translatable within body (222) between a proximal longitudinal position and a distal longitudinal position. Yoke (290) is supported in handle assembly (220) by rails (not shown) formed in body (222) of handle assembly (220), such that yoke (290) is constrained to longitudinal movement within handle assembly (220). Because the proximal portion of trigger (228) is coupled with yoke (290) via link (229), it should be understood that pivoting of trigger (228) toward pistol grip (224) will cause proximal longitudinal translation of yoke (290) within body (222); and that pivoting of trigger (228) away from pistol grip (224) will cause distal longitudinal translation of yoke (290) within body (222). As will be discussed in more detail below, longitudinal translation of yoke (290) between the proximal longitudinal position and the distal longitudinal position pumps liquid coolant from fluid reservoir (270) to end effector (240) via fluid pump (280).

B. Exemplary Piston Pump for Ultrasonic Surgical Instrument

Figure 11:
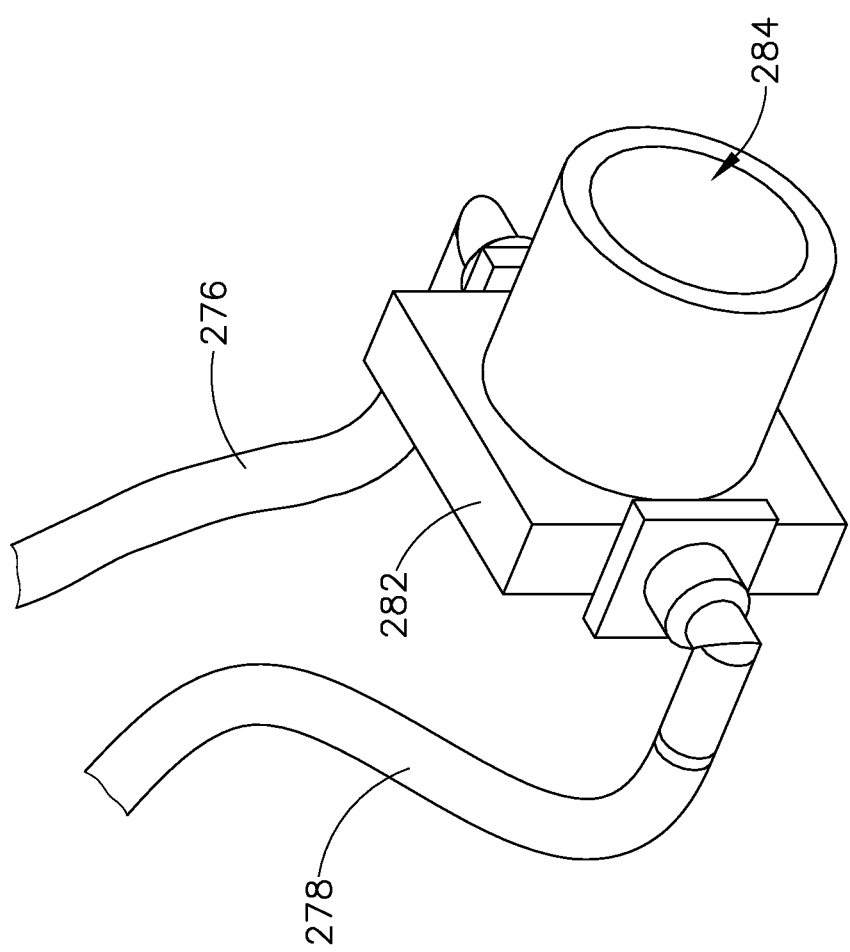
FIG. 11 depicts a perspective view of a pump of the instrument of FIG. 5.

FIGS. 10-14C depict fluid pump (280) of the present example in greater detail. As best seen in FIG. 11, fluid pump (280) comprises a pump body (282) that is coupled to first tube (276) and a second tube (278). First tube (276) is further coupled with fluid reservoir (270) as noted above. As will be discussed in more detail below, second tube (278) is in fluid communication with shaft assembly (230) via a knob assembly (300). As will also be discussed in more detail below, shaft assembly (230) is operable to deliver the liquid coolant from second tube (278) and knob assembly (300) to end effector (240). Pump body (282) defines a hollow cylindrical interior (284) that is configured to receive a piston (292) of a plunger (291) of yoke (290).

In the present example, hollow cylindrical interior (284) is in fluid communication with first tube (276) and second tube (278) via a pair of one-way valves. A first one-way valve permits the flow of liquid coolant from first tube (276) into hollow cylindrical interior (284) of pump body (282) but not in the opposite direction. A second one-way valve permits the flow of liquid coolant from hollow cylindrical interior (284) of pump body (282) into second tube (278) but not in the opposite direction. Thus, the one-way valves permit the flow of liquid coolant from first tube (276) through pump body (282) and from pump body (282) into second tube (278); but prohibit the flow of liquid coolant from second tube (278) into pump body (282) and from pump body (282) into first tube (276). It should therefore be understood that the one-way valves permit the flow of liquid coolant from fluid reservoir (270) to knob assembly (300) via fluid pump (280), but not vice versa. Various suitable kinds of valves that may be used will be readily apparent to those of ordinary skill in the art.

Figure 12:
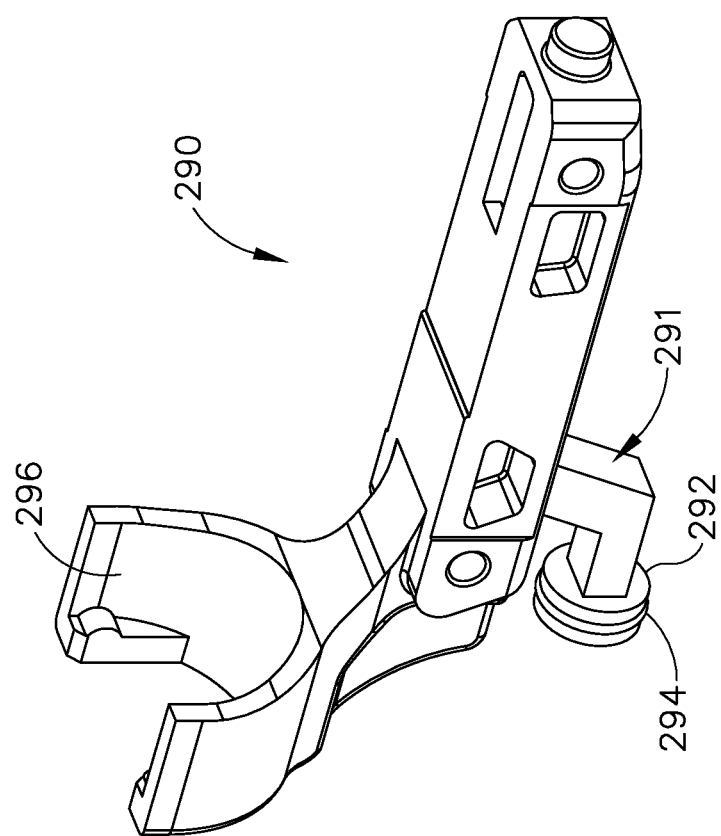
FIG. 12 depicts a perspective view of a yoke of the instrument of FIG. 5.
Figure 13:
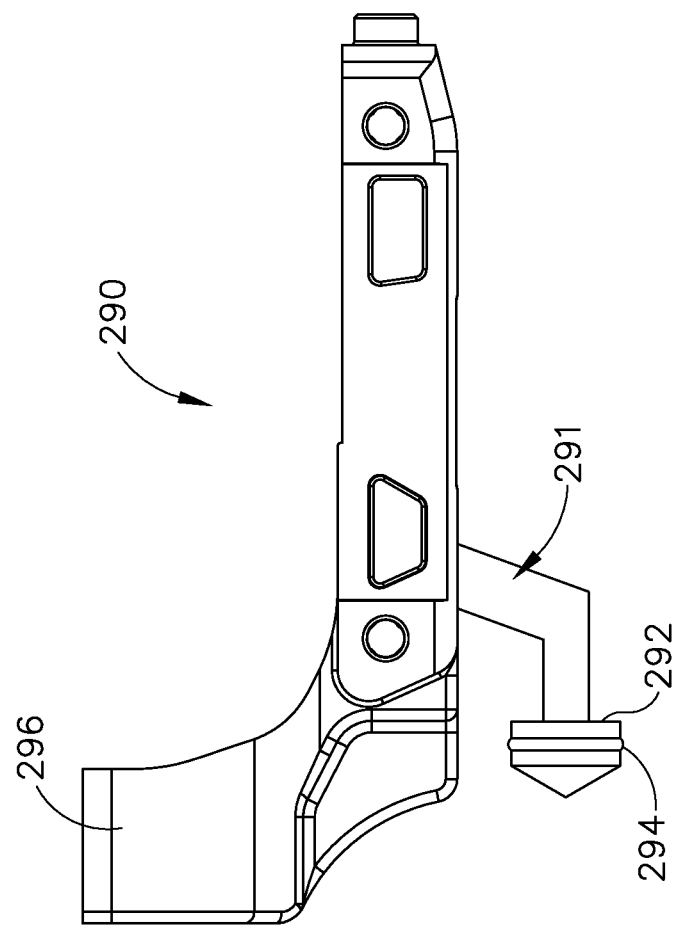
FIG. 13 depicts a side elevational view of the yoke of FIG. 12.

As shown in FIGS. 12-13, yoke (290) comprises a fork feature (296) and a plunger (291). Fork feature (296) is configured to couple with complementary feature at the proximal end of an inner tube (234) of shaft assembly (230), such that yoke (290) and inner tube (234) longitudinally translate together unitarily. Plunger (291) extends from a bottom surface of yoke (290) and includes an integral piston (292). As mentioned above, hollow cylindrical interior (284) of pump body (282) is configured to receive piston (292) of plunger (291). Piston (292) comprises a circular seal ring (294) that is configured to engage an interior surface of hollow cylindrical interior (284) to thereby provide a fluid seal between an interior surface of pump body (282) and piston (292). As discussed above, yoke (290) is longitudinally translatable within body (222) between a proximal longitudinal position and a distal longitudinal position. Longitudinal translation of yoke (290) between the proximal longitudinal position and the distal longitudinal position causes concurrent longitudinal translation of piston (292) within pump body (282). As will be described in more detail below, this longitudinal translation of piston (292) is causes a pumping effect within pump body (282). In the present example, as shown in FIGS. 7-8 and 14A-14C, a coil spring (291) is positioned proximal to yoke (290) and resiliently biases yoke (290) distally. Of course, yoke (290) may be resiliently biased in any other suitable fashion; or may be non-biased if desired.

Figure 14A:
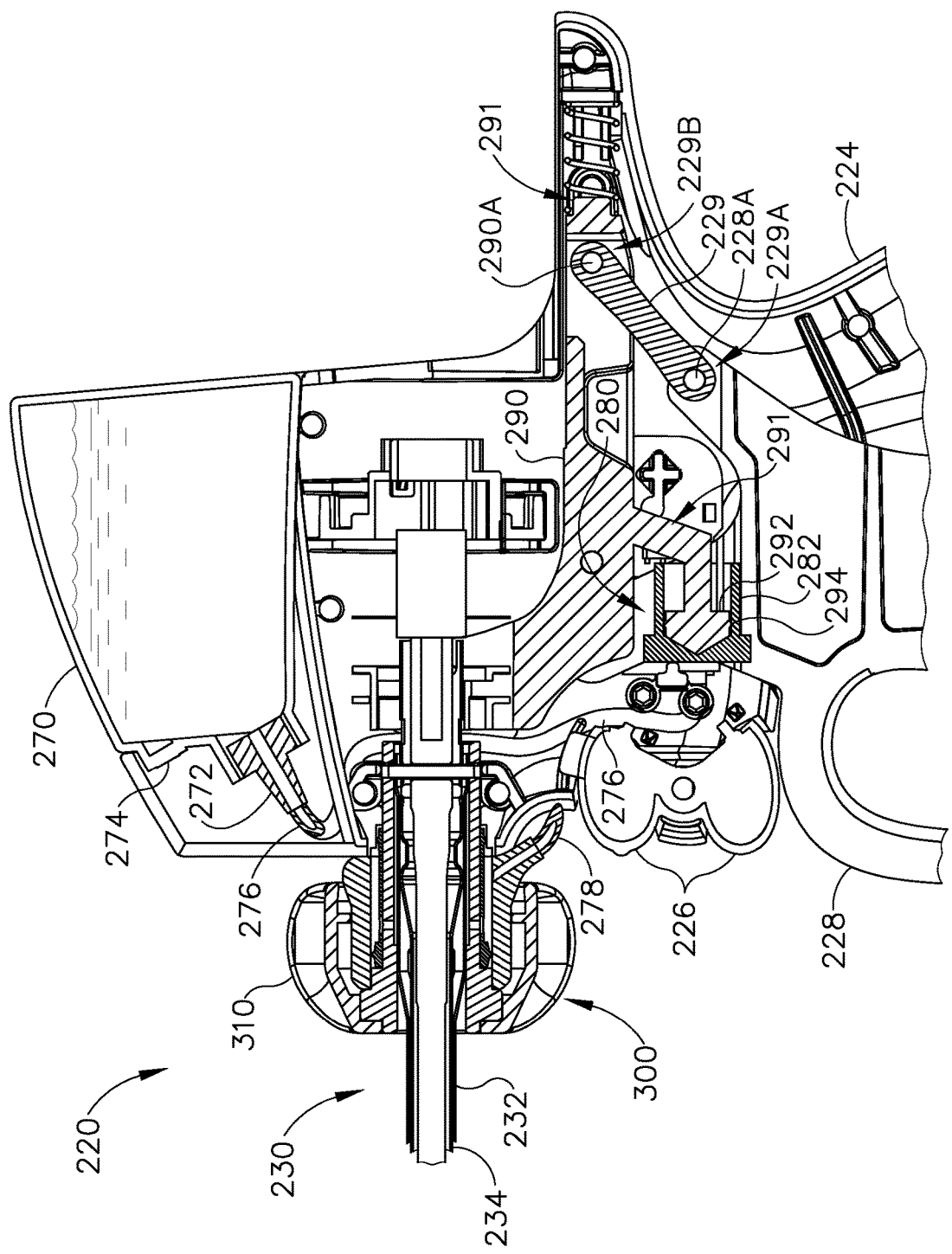
FIG. 14A depicts a side elevational view of the handle assembly of FIG. 6 with the housing shroud of FIG. 7 removed, with the trigger of the handle assembly in a first rotational position, and with the yoke of FIG. 12 in a first longitudinal position.
Figure 14B:
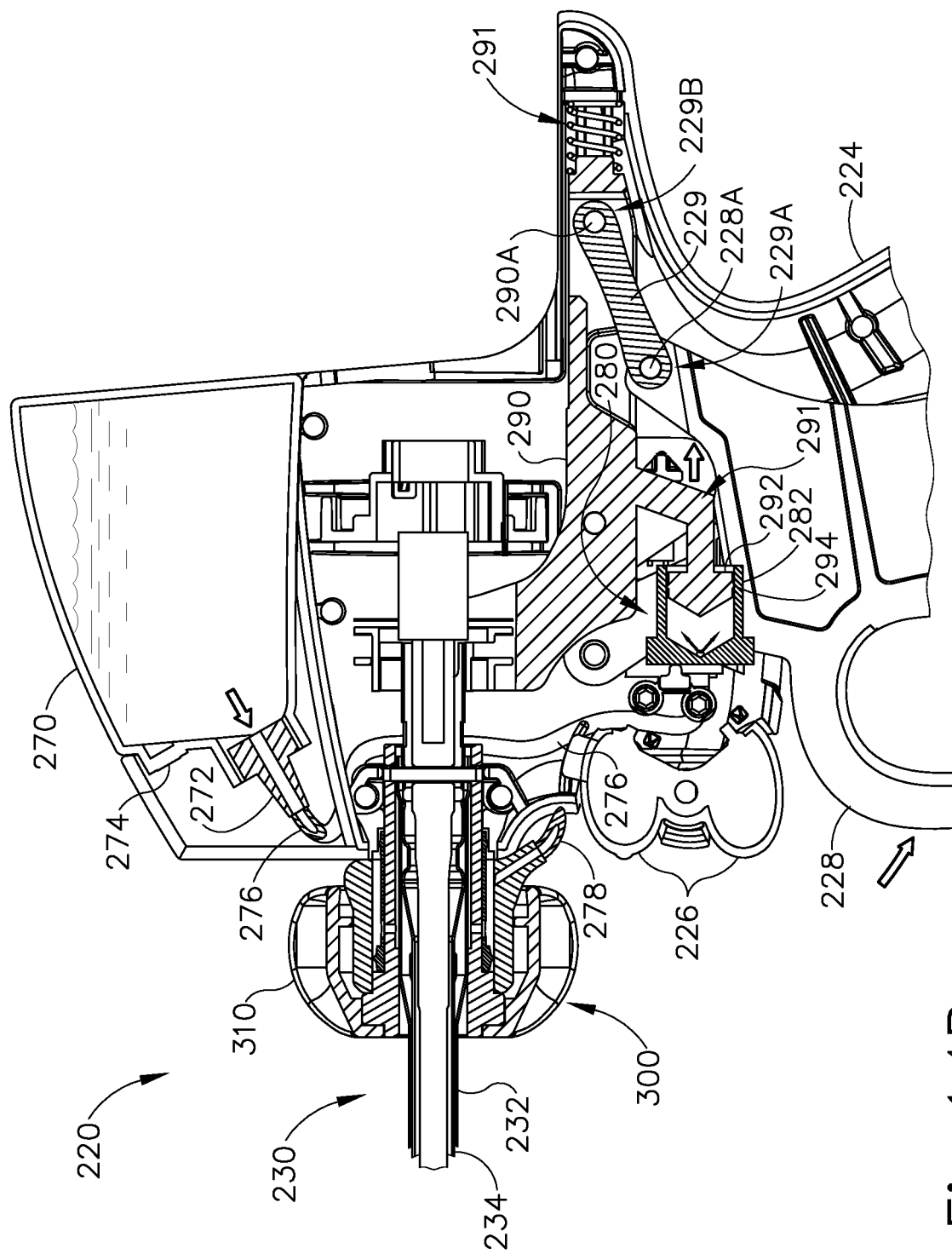
FIG. 14B depicts a side elevational view of the handle assembly of FIG. 6 with the housing shroud of FIG. 7 removed, with the yoke of FIG. 12 moved to a second longitudinal position by movement of the trigger to a second rotational position to thereby draw fluid from the fluid reservoir into the pump of FIG. 11.
Figure 14C:
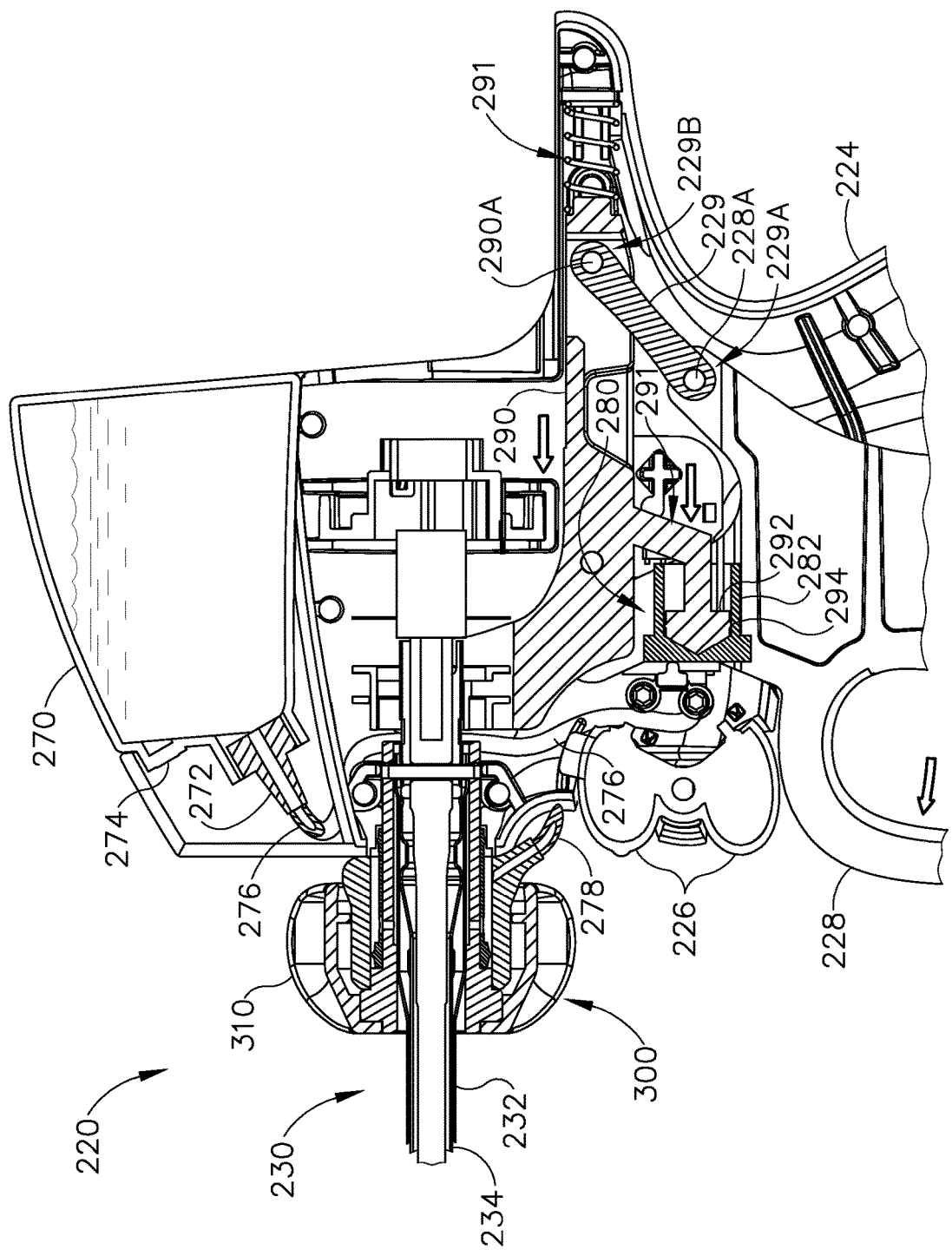
FIG. 14C depicts a side elevational view of the handle assembly of FIG. 6 with the housing shroud of FIG. 7 removed, with the yoke of FIG. 12 moved back into the first longitudinal position by movement of the trigger back to the first rotational position to thereby force fluid from the pump of FIG. 11.

FIGS. 14A-14C depict the operation of fluid pump (280). FIG. 14A shows instrument (200) in an initial configuration. At this stage, trigger (228) is positioned distally in relation to pistol grip (224); and clamp arm (244) is pivoted away from blade (260) such that end effector (240) is in an open configuration. As shown in FIG. 14B, and as discussed above, pivoting of trigger (228) toward pistol grip (224) causes proximal longitudinal translation of yoke (290) within body (222) which in turn causes proximal longitudinal translation of piston (292) within pump body (282). The proximal translation of yoke (290) within body (222) also causes proximal translation of inner tube (234), which in turn causes clamp arm (244) to pivot toward blade (260) such that end effector (240) is in a closed configuration. The proximal longitudinal translation of piston (292) within pump body (282) causes a vacuum to be drawn within pump body (282) thereby drawing liquid coolant from fluid reservoir (270) into pump body (282) via first tube (276).

As shown in FIG. 14C, and as discussed above, pivoting of trigger (228) away from pistol grip (224) from a proximal position back to the distal position causes distal longitudinal translation of yoke (290) within body (222), which in turn causes distal longitudinal translation of piston (292) within pump body (282). The distal translation of yoke (290) within body (222) also causes distal translation of inner tube (234), which in turn causes clamp arm (244) to pivot away from blade (260) such that end effector (240) is again in the open configuration. The distal longitudinal translation of piston (292) within pump body (282) pressurizes the liquid coolant within hollow cylindrical interior (284) of pump body (282), thereby forcing liquid coolant from pump body (282) into second tube (278). It should be appreciated that the one-way valve at the coupling between first tube (276) and pump body (282) prohibits liquid coolant being forced into first tube (276) as piston (292) pressurizes the liquid coolant within pump body (282). Thus, it should be understood that pivoting of trigger (228) toward and away from pistol grip (224) will pump liquid coolant from fluid reservoir (270) to knob assembly (300) via fluid pump (280); while simultaneously pivoting clamp arm (244) toward and away from blade (260). It should also be appreciated that at the coupling between second tube (278) and pump body (282) prohibits liquid coolant in second tube (278) from being pumped into pump body (282).

It should be understood that the above described example of fluid pump (280) just represents one merely illustrative form that fluid pump (280) may take. By way of example only, fluid pump (280) may instead be constructed and configured in accordance with at least some of the teachings of U.S. patent application Ser. No. 14/553,329, entitled "Features to Drive Fluid toward an Ultrasonic Blade of a Surgical Instrument," filed on Nov. 25, 2014, issued as U.S. Pat. No. 10,004,529 on Jun. 26, 2018, the disclosure of which is incorporated by reference herein. As another merely illustrative example, fluid pump (280) (or some variation thereof) may be located between trigger (228) and pistol grip (227) such that trigger (228) directly drives the fluid pump (280). As yet another merely illustrative example, fluid pump (280) (or some variation thereof) may be located at the proximal end of yoke (290), such that fluid pump (280). In some such versions, fluid pump (280) is actuated by proximal movement of yoke (290). Other suitable ways in which fluid pump (280) may be configured and operable will be apparent to those of ordinary skill in the art in view of the teachings herein.

Similarly, while fluid pump (280) is integrated with body (222) in this example, it should be understood that fluid pump (280) may be separate from body (222). For instance, fluid pump (280) may comprise a conventional fluid pump that is coupled with second tube (278) via a conduit. As another merely illustrative alternative, fluid pump (280) may be incorporated into ultrasonic generator (12) or some other piece of capital equipment. Other suitable locations for a fluid pump will be apparent to those of ordinary skill in the art in view of the teachings herein.

C. Exemplary Knob Assembly with Fluid Manifold

Figure 16:
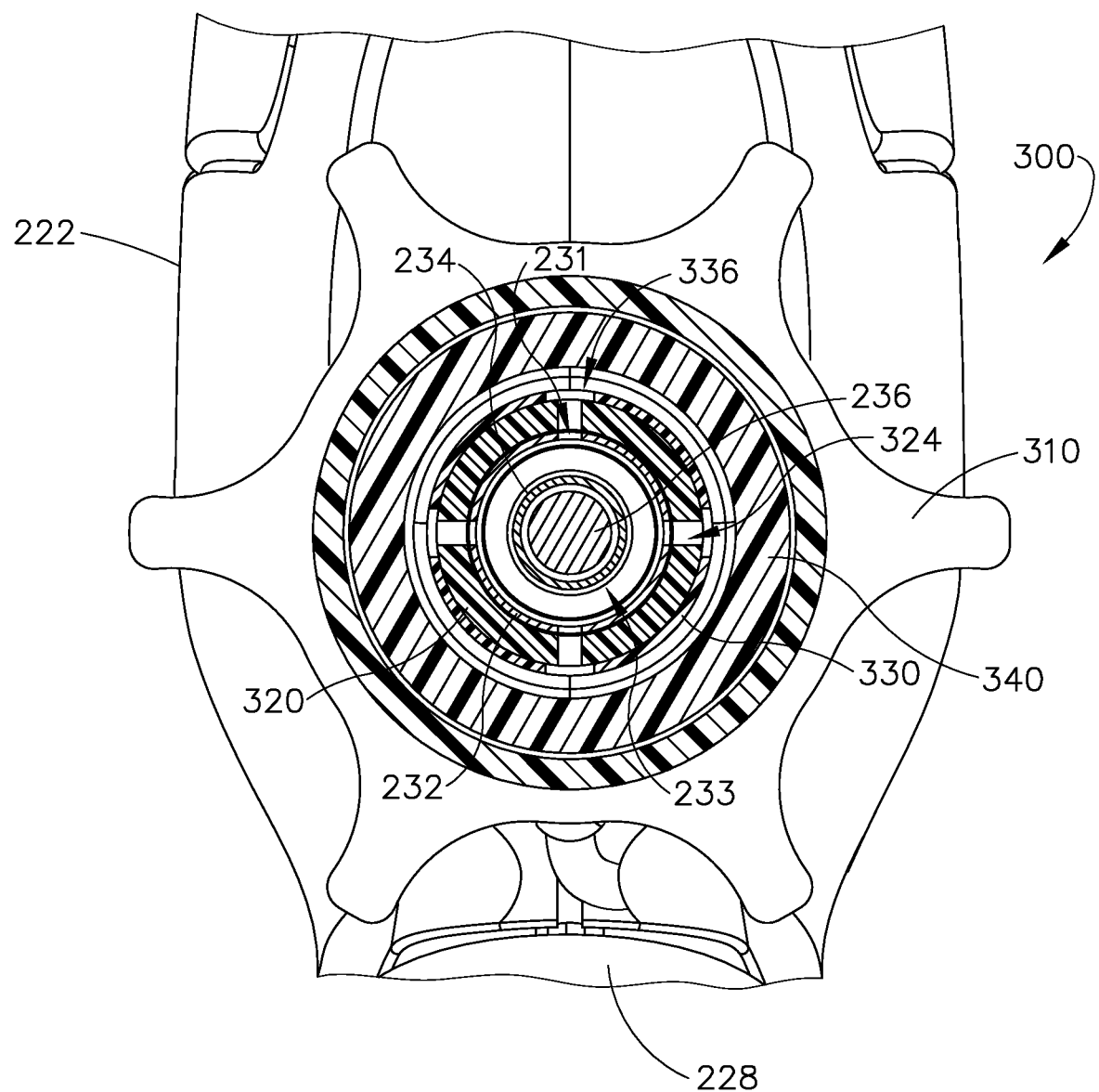
FIG. 16 depicts a detailed cross-sectional end view of the handle assembly of FIG. 6, taken along line 16-16 of FIG. 15.
Figure 17:
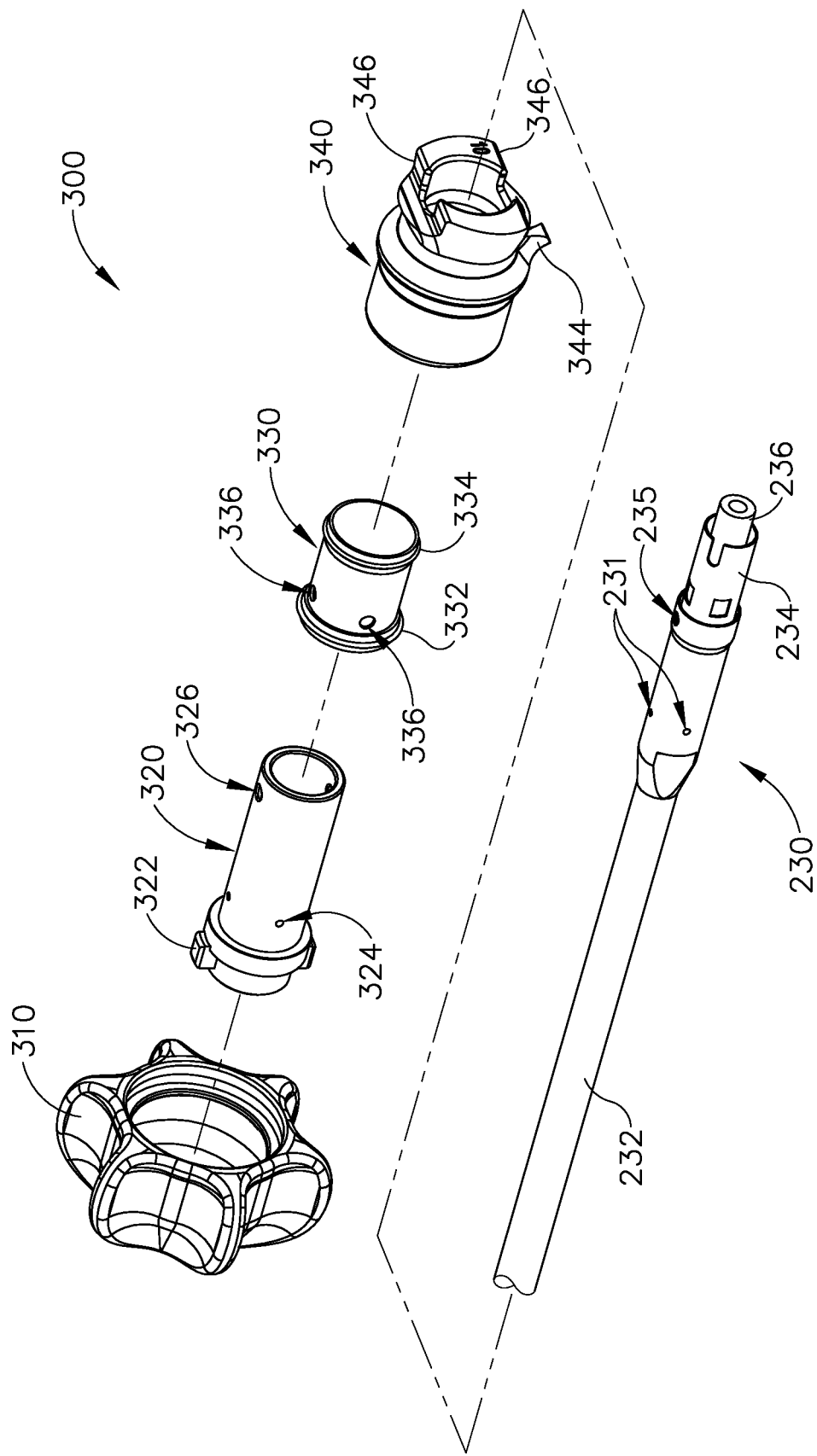
FIG. 17 depicts an exploded perspective view of a knob assembly at the proximal end of a shaft assembly of the instrument of FIG. 5.
Figure 18:
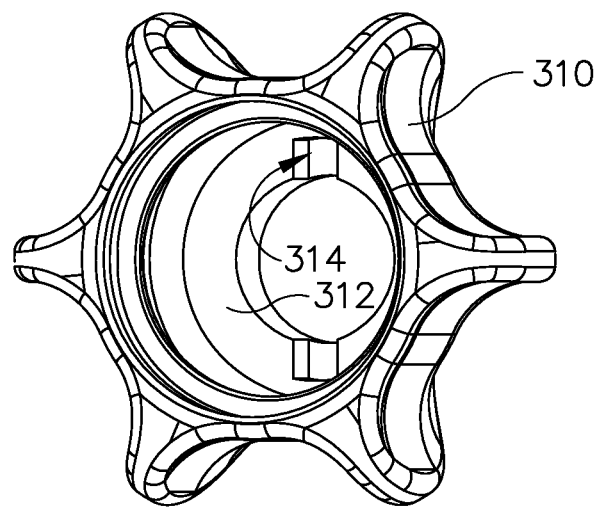
FIG. 18 depicts a perspective view of a rotation knob of the knob assembly of FIG. 17.
Figure 19:
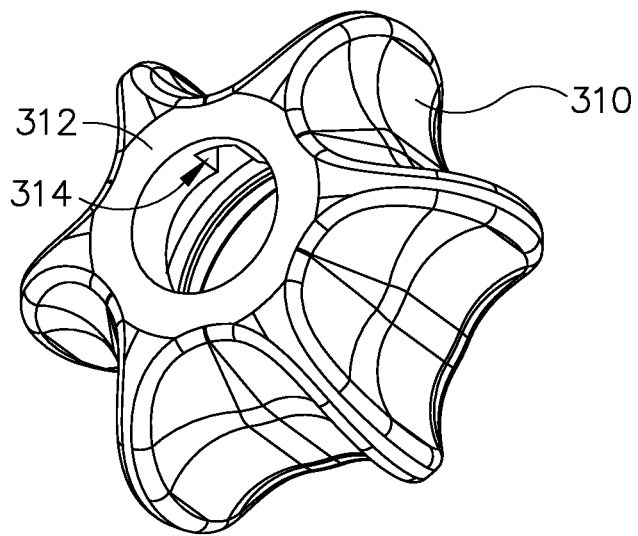
FIG. 19 depicts another perspective view of the rotation knob of FIG. 17.
Figure 20:
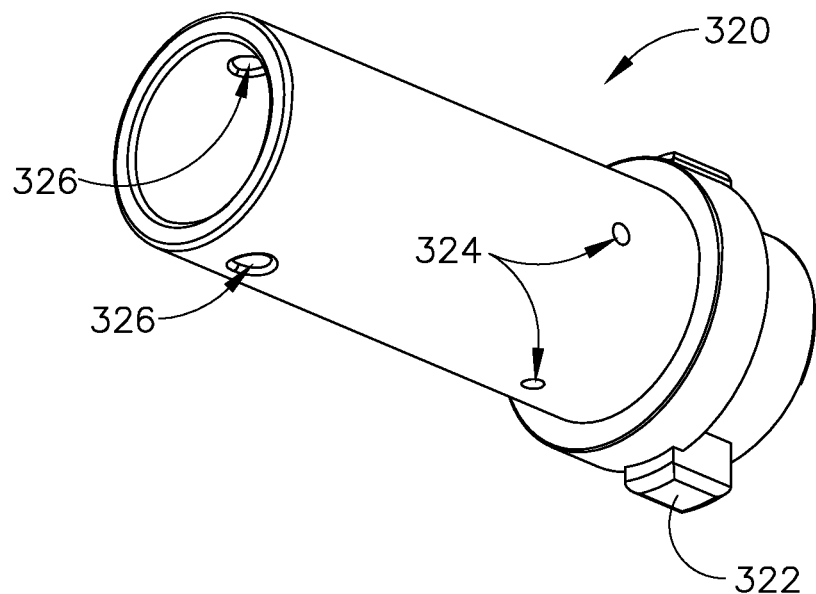
FIG. 20 depicts a perspective view of an inner housing of the knob assembly of FIG. 17.
Figure 21:
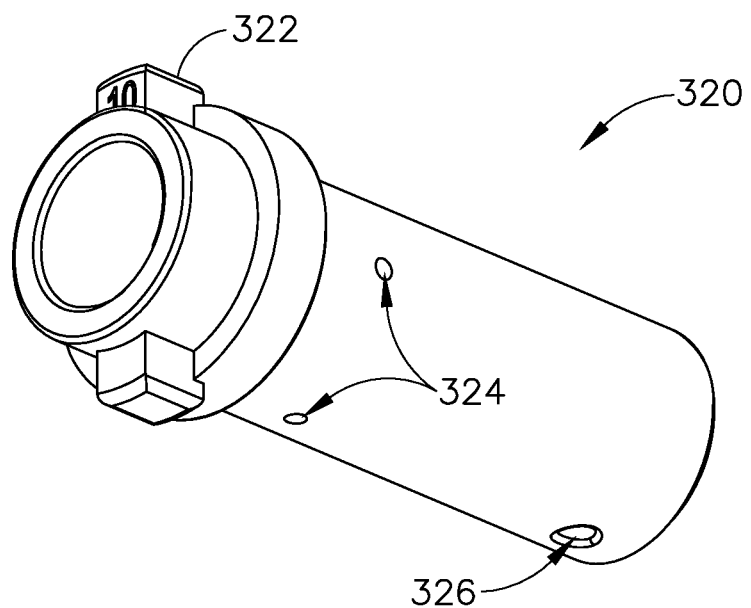
FIG. 21 depicts another perspective view of the inner housing of FIG. 20.
Figure 22:
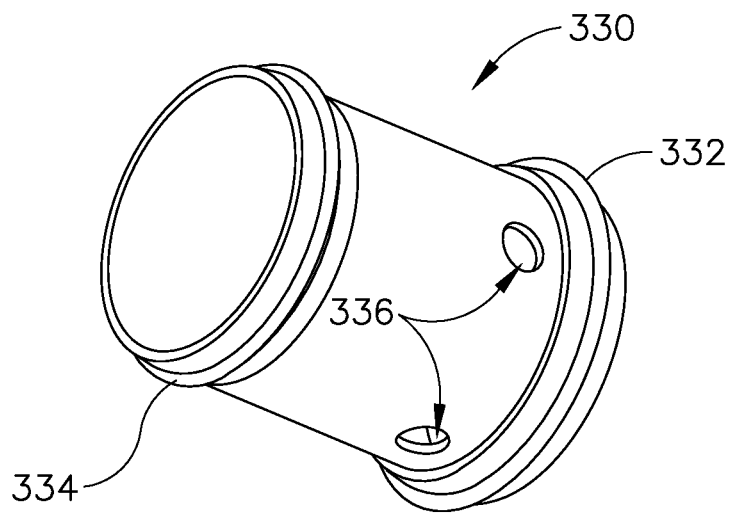
FIG. 22 depicts a perspective view of a sealing member of the knob assembly of FIG. 17.
Figure 23:
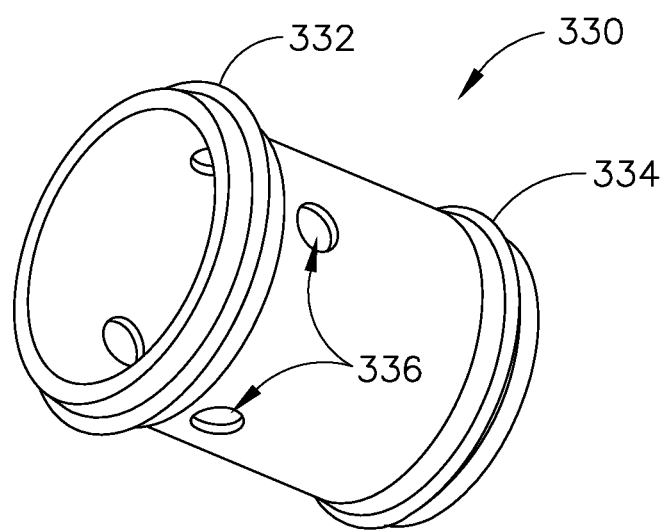
FIG. 23 depicts another perspective view of the sealing member of FIG. 22.
Figure 24:
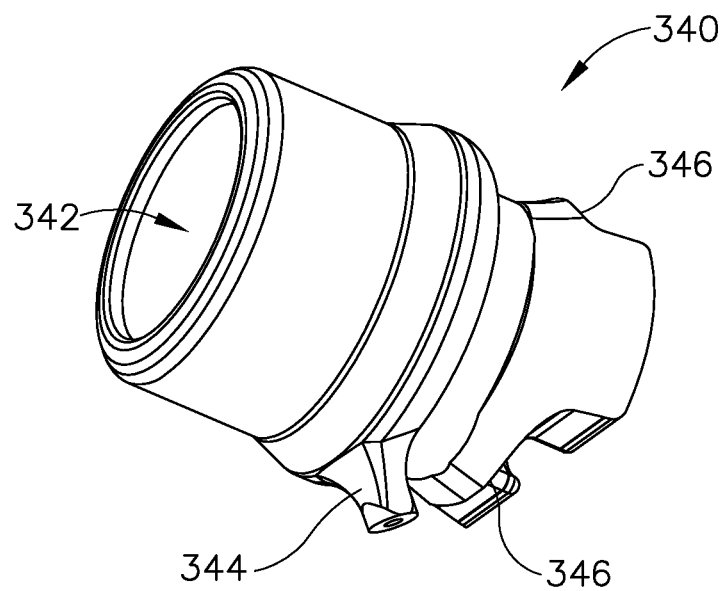
FIG. 24 depicts a perspective view of a manifold housing of the knob assembly of FIG. 17.
Figure 25:
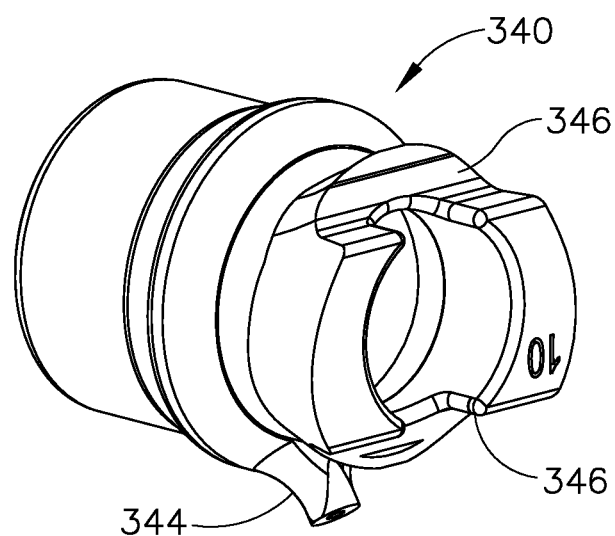
FIG. 25 depicts another perspective view of the manifold housing of FIG. 24.
Figure 26:
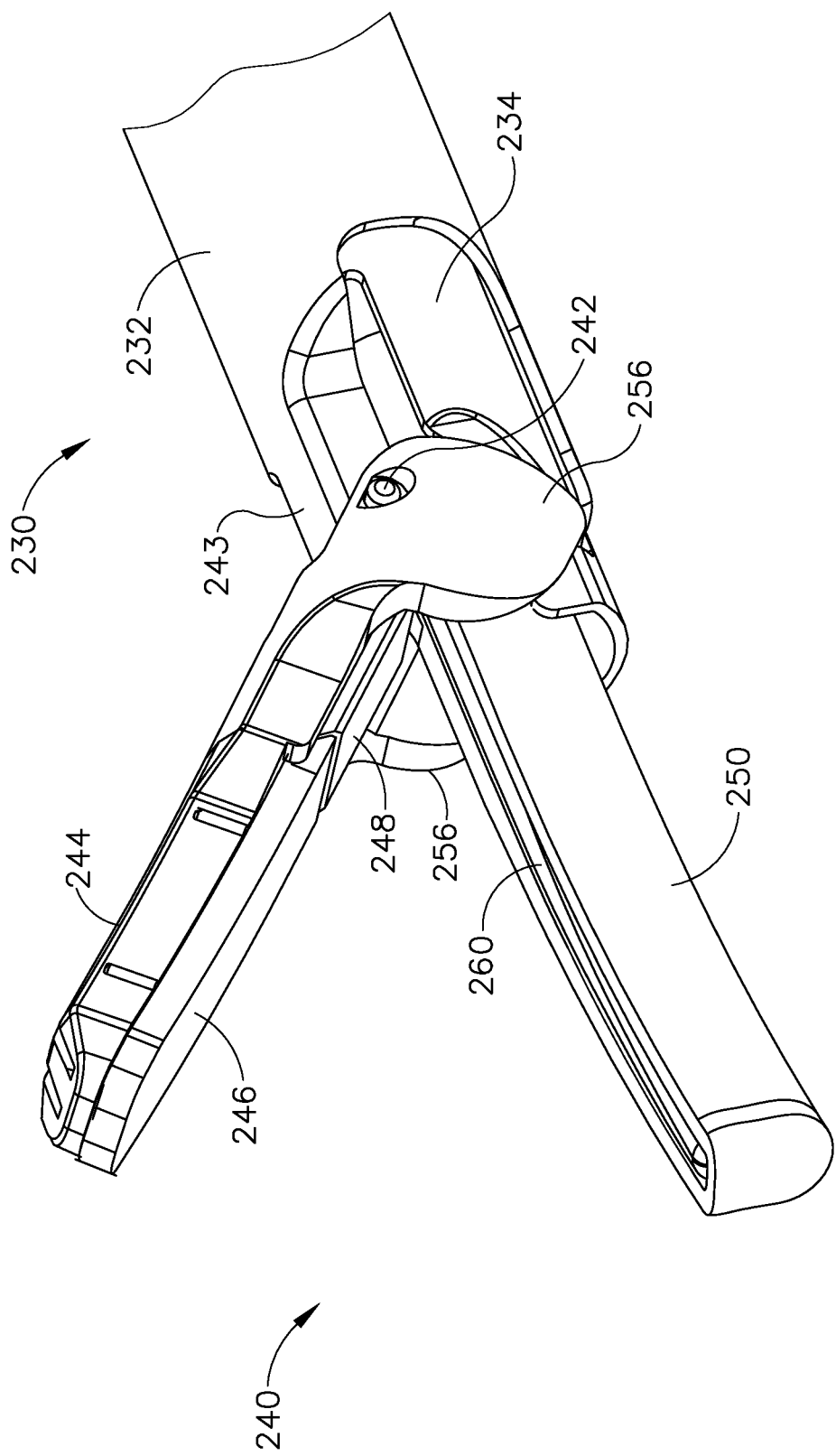
FIG. 26 depicts a perspective view of an end effector of the instrument of FIG. 5.

As discussed above, shaft assembly (230) comprises outer sheath (232) and inner tube (234). Shaft assembly (230) further comprises an acoustic waveguide (236) extending coaxially through inner tube (234). A knob assembly (300) is secured to the proximal end of shaft assembly (230). FIGS. 15-17 show knob assembly (300) in greater detail. As shown, knob assembly (300) comprises an outer knob (310), a rotatable manifold (320), a seal sleeve (330), and a stationary manifold (340). All of these components are coaxially aligned with shaft assembly (230). Outer knob (310) is exposed and is operable to rotate the entire shaft assembly (230) and end effector (240) relative to handle assembly (220) about a longitudinal axis of shaft assembly (230). As best seen in FIGS. 18-19, outer knob (310) has a distal wall (312) with a pair of key recesses (314) formed in the proximal face of distal wall (312). As best seen in FIGS. 15 and 20-21, rotatable manifold (320) includes a pair of keys (322) that are configured to fit in key recesses (314) of outer knob (310). Outer knob (310) and rotatable manifold (320) are thus configured to rotate unitarily about the longitudinal axis of shaft assembly (230).

As also shown in FIGS. 15-17 and 20-21, rotatable manifold (320) further includes a set of four fluid openings (324) near the distal end of rotatable manifold (320) and a pair of pin openings (326) near the proximal end of rotatable manifold (320). Rotatable manifold (320) is configured to fit about the proximal end of outer sheath (232). With rotatable manifold (320) disposed about outer sheath (232), fluid openings (324) are aligned with complementary fluid openings (231) that are formed at the proximal end of outer sheath (232). Openings (231, 324) thus cooperate to provide pathways for communication of liquid coolant as will be described in greater detail below. While four complementary openings (231, 324) are provided in the present example, it should be understood that less than four or more than four may be provided, if desired. Also when rotatable manifold (320) disposed about outer sheath (232), pin openings (326) are aligned with complementary pin openings (235) that are formed at the proximal end of outer sheath (232). As best seen in FIG. 15, a pin (239) is disposed in pin openings (235, 326). Pin (239) is also disposed in waveguide (236). Pin (239) thus secures rotatable manifold (320), outer sheath (232), and waveguide (236) together such that rotatable manifold (320), outer sheath (232), and waveguide (236) will all rotate together unitarily about the longitudinal axis of shaft assembly (230). In the present example, pin (239) is located at a longitudinal position corresponding to a node associated with resonant ultrasonic vibrations communicated through waveguide (236). The ultrasonic vibrations are thus not communicated to rotatable manifold (320) or outer sheath (232).

As shown in FIGS. 15-17 and 22-23, seal sleeve (330) comprises a distal sealing member (332), a proximal sealing member (334), and a set of four fluid openings (336) between sealing members (332, 334). Seal sleeve (330) is configured to fit snugly about rotatable manifold (320). With seal sleeve (330) positioned about rotatable manifold (320), fluid openings (336) align with fluid openings (231, 324) of outer sheath (232) and rotatable manifold (320), such that openings (231, 324, 336) cooperate to provide pathways for communication of liquid coolant as will be described in greater detail below.

As shown in FIGS. 15, 17, and 24-25, stationary manifold (340) defines a hollow interior (342) and includes a fluid port (344) that is in fluid communication with hollow interior (342). The proximal end of stationary manifold (340) includes a pair of seats (346) that are configured to engage fixed bosses (223) of body (222), as best seen in FIG. 15. This engagement prevents stationary manifold (340) from rotating within body (222). It should be understood that the proximal end of stationary manifold (340) is located distal to pin (239), such that stationary manifold (340) does not engage pin (239) or otherwise restrict rotation of shaft assembly (230) about the longitudinal axis of shaft assembly (230). Seal sleeve (330), rotatable manifold (320), and the proximal end of shaft assembly (230) are all disposed in hollow interior (342). As shown in FIG. 15, sealing members (332, 334) are configured to engage the inner sidewall of hollow interior (342), thereby sealing the region of hollow interior (342) between sealing members (332, 334). Sealing members (332, 334) maintain this seal even as seal sleeve (330), rotatable manifold (320), and shaft assembly (230) are rotated within stationary manifold (340) about the longitudinal axis of shaft assembly (230). Seal sleeve (330) is sized to maintain a gap within this region of hollow interior (342) between sealing members (332, 334). As also shown in FIG. 15, fluid port (344) is in fluid communication with the gap in this region of hollow interior (342) between sealing members (332, 334). Fluid port (344) is also in fluid communication with second tube (278). As described above, second tube (278) serves as a fluid outlet for fluid pump (280). Fluid pump (280) is thus in fluid communication with the gap in the region of hollow interior (342) between sealing members (332, 334).

It should be understood from the foregoing that, as fluid pump (280) is actuated to drive liquid coolant through second tube (278), second tube (278) passes the liquid coolant through stationary manifold (340) and into hollow interior (342). The liquid coolant then travels through openings (336, 324, 231) to reach an interior space (233) that is defined between outer sheath (234) and inner tube (234). As will be described in greater detail below, the liquid coolant travels along the length of shaft assembly (230) through this interior space (233) to reach end effector (240), where the liquid coolant ultimately cools blade (260).

D. Exemplary End Effector with Ultrasonic Blade Quenching Sleeve

FIGS. 26-29 show end effector (240) in greater detail. End effector (240) is positioned at the distal end of shaft assembly (230). As noted above, end effector (244) comprises an ultrasonic blade (260) and a pivoting clamp arm (244). As further discussed above, shaft assembly (230) of the present example comprises an outer sheath (232) and an inner tube (234). Inner tube (234) is slidably disposed within outer sheath (232). As with shaft assembly (130) discussed above, inner tube (234) is operable to translate longitudinally within outer sheath (232) relative to outer sheath (232) to selectively pivot clamp arm (244) toward and away from blade (260).

Clamp arm (244) of the present example includes a primary clamp pad (246) and a secondary clamp pad (248) that are secured to the underside of clamp arm (244), facing blade (260). Clamp arm (244) is pivotably secured to a distally projecting tongue (243) of outer sheath (232) via a pin (242). Clamp arm (244) is operable to selectively pivot toward and away from blade (260) to selectively clamp tissue between clamp arm (244) and blade (260). A pair of arms (256) extend transversely from clamp arm (244) and are secured to a distal portion (270) of inner tube (276) that extends laterally between arms (256). Thus, as with shaft assembly (130) discussed above, longitudinal translation of inner tube (234) causes rotation of clamp arm (244) toward and away from blade (260).

Figure 27:
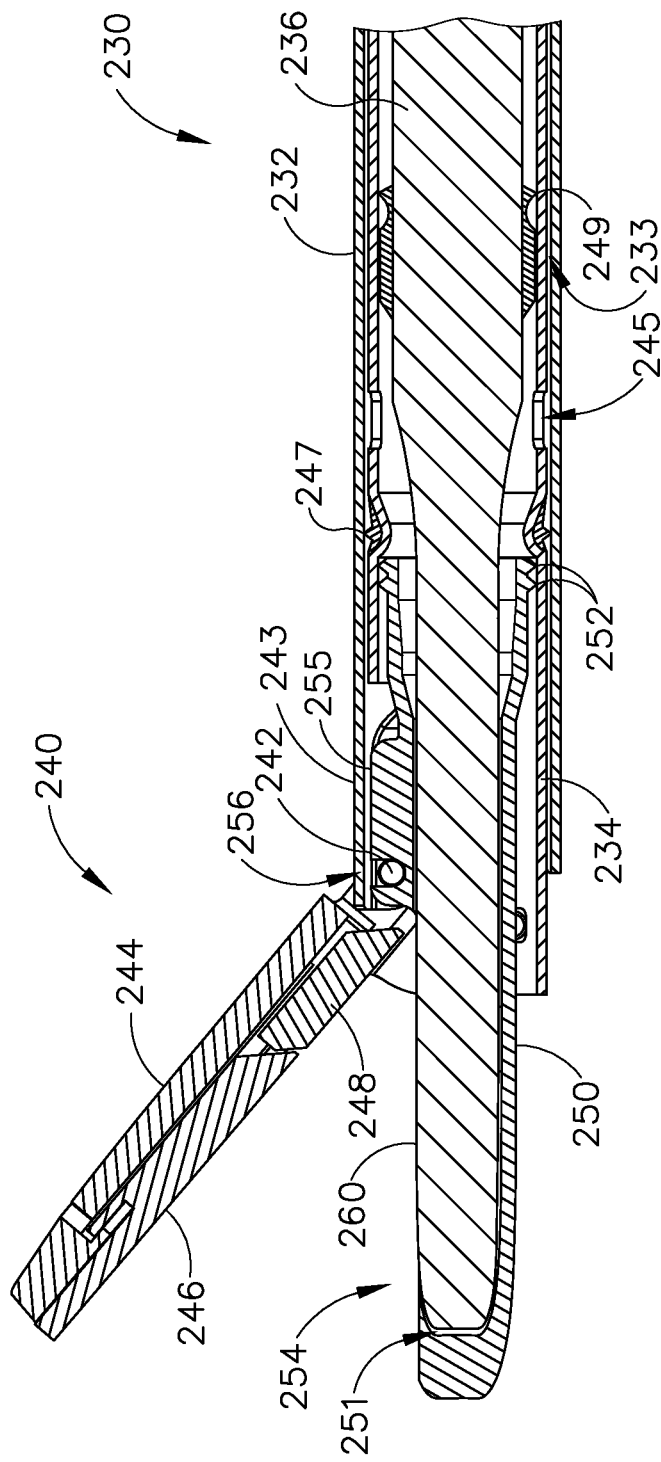
FIG. 27 depicts a cross-sectional side view of the end effector of FIG. 26.
Figure 28:
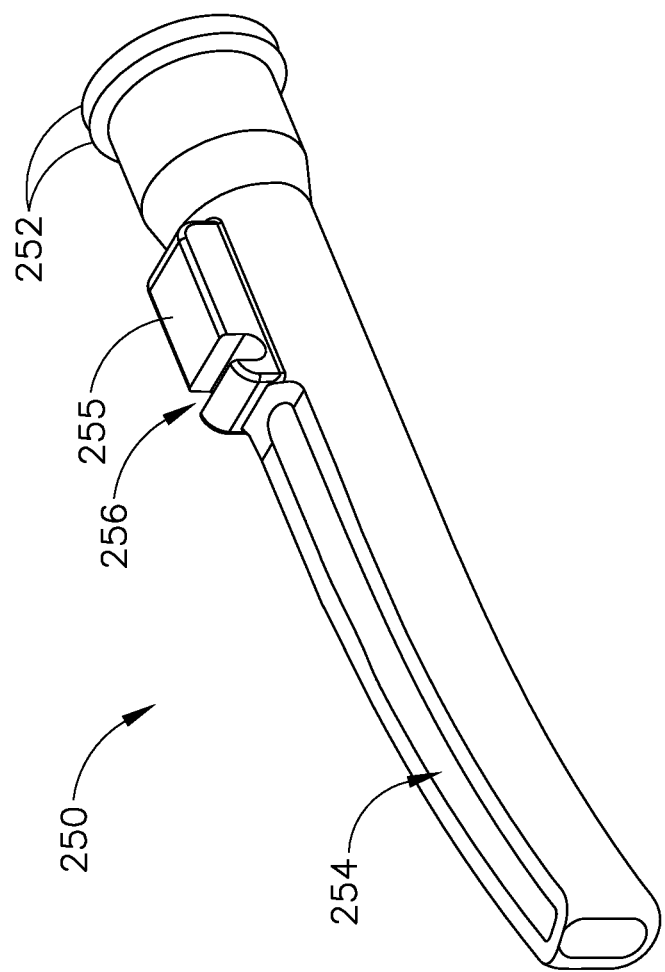
FIG. 28 depicts a perspective view of a sleeve of the end effector of FIG. 26.
Figure 29:
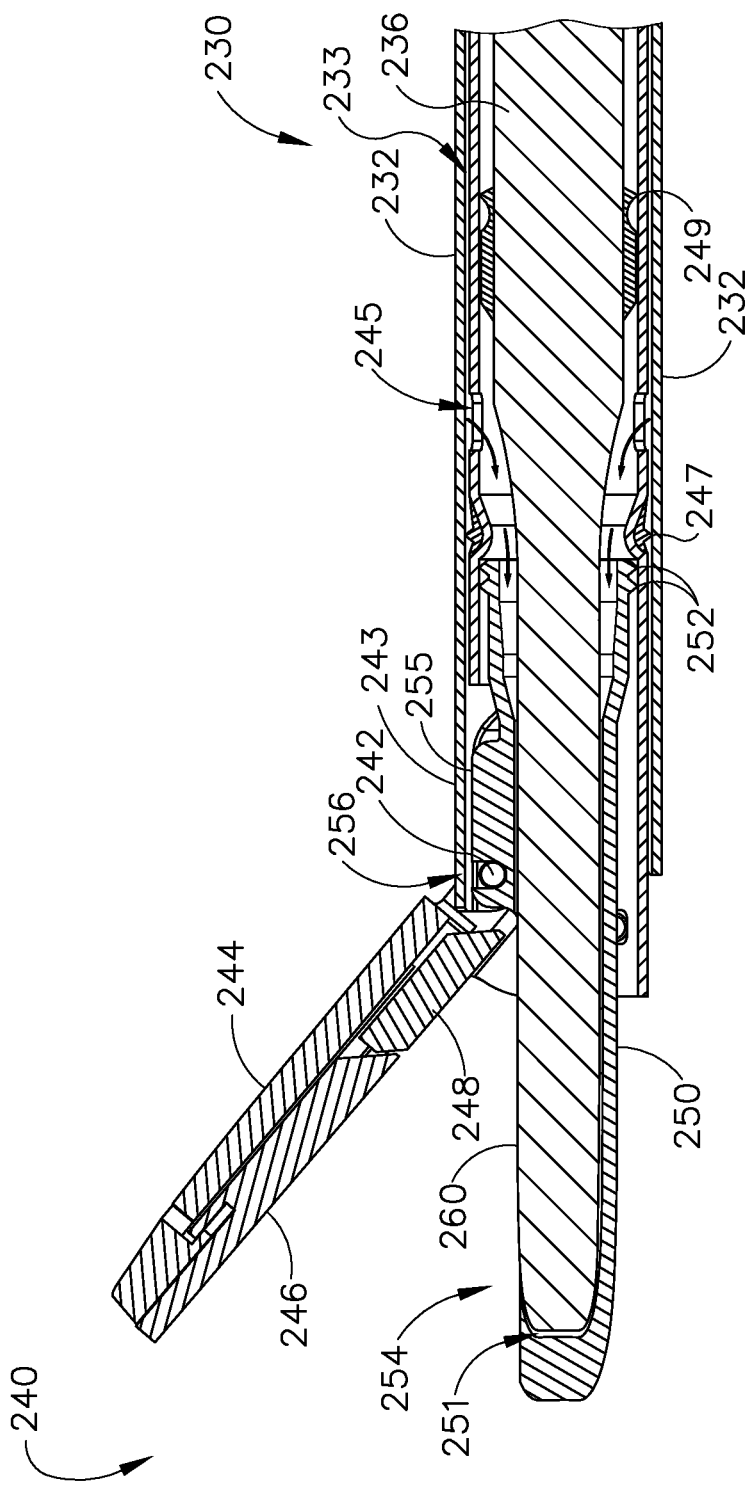
FIG. 29 depicts a cross-sectional side view of the end effector of FIG. 26, with fluid forced from the pump of FIG. 11 passing through the interior passageway of the shaft assembly and into the sleeve.

End effector (240) of the present example further comprises a sleeve (250). As shown in FIGS. 27 and 29, a proximal end of sleeve (250) is disposed within a distal end of inner tube (234). As best seen in FIGS. 27-29, a proximal end of sleeve (250) comprises a pair of annular seals (252) that are configured to engage an interior surface of inner tube (234) to thereby provide a fluid seal between inner tube (234) and sleeve (250). Annular seals (252) further provide a friction fit between inner tube (234) and sleeve (250) such that sleeve (250) is selectively secured within inner tube (234). Sleeve (250) further comprises a projection (255) having a slot (256) formed therein. Slot (256) is configured to receive pin (242) to thereby longitudinally retain sleeve (250) relative to inner tube (234). Thus, sleeve (250) remains stationary as inner tube (234) translates longitudinally to drive clamp arm (244) toward and away from blade (260). Sleeve (250) also defines a curved channel (254) having a closed distal end. Channel (254) is configured to receive blade (260). Channel (254) is sized slightly larger than blade (260) in order to provide a gap (251) between the inner surface of sleeve (250) that defines gap (251) and the outer surface of blade (260). As will be discussed in more detail below, channel (254) is configured to receive liquid coolant from fluid pump (280) such that the liquid coolant is placed in contact with blade (260) via gap (251) to thereby cool blade (260).

In some versions, sleeve (250) may comprise a silicone material. In some such versions, one or more features are included to provide structural reinforcement to sleeve (250), to reduce or eliminate deflection of sleeve (250) relative to the longitudinal axis of blade (260). By way of example only, sleeve (250) may be configured and operable in accordance with at least some of the teachings of U.S. patent application Ser. No. 14/552,552, entitled "Shielding Features for Ultrasonic Blade of a Surgical Instrument," filed on Nov. 25, 2014, issued as U.S. Pat. No. 9,993,260 on Jun. 12, 2018, the disclosure of which is incorporated by reference herein; U.S. patent application Ser. No. 14/552,681, entitled "Sleeve Features for Ultrasonic Blade of a Surgical Instrument," filed on Nov. 25, 2014, issued as U.S. Pat. No. 10,004,528 on Jun. 26, 2018, the disclosure of which is incorporated by reference herein; and/or U.S. patent application Ser. No. 14/553,329, entitled "Features to Drive Fluid toward an Ultrasonic Blade of a Surgical Instrument," filed on Nov. 25, 2014, issued as U.S. Pat. No. 10,004,529 on Jun. 26, 2018, the disclosure of which is incorporated by reference herein. It should therefore be understood that sleeve (250) may serve as a heat shield for blade (260) in addition to providing structure to assist in liquid cooling of blade (260).

As discussed above, fluid pump (280) is operable to drive liquid coolant into interior space (233) of shaft assembly (230) via knob assembly (300). As shown in FIG. 29, as liquid coolant is passed within interior space (233) of shaft assembly (230), the liquid coolant travels the length of shaft assembly (230) and eventually passes from interior space (233) into an interior of inner tube (234) via a set of openings (245) that are formed in a distal portion of inner tube (234). Again, any suitable number of openings (245) may be provided. A fluid seal (247) is interposed between the distal end of inner tube (234) and the inner surface of outer sheath (232). Fluid seal (247) thus prevents the fluid from inadvertently escaping interior space (233) distally. As discussed above, a proximal end of sleeve (250) is disposed within a distal end of inner tube (234). Annular seals (252) are configured to engage an inner surface of inner tube (234) to thereby provide a fluid seal between inner tube (234) and sleeve (250) such that liquid coolant is configured to pass from the interior of inner tube (234) to the gap (251) in channel (254) of sleeve (250). Another fluid seal (249) is interposed between waveguide (236) and the inner surface of inner tube (234). Fluid seal (249) thus prevents fluid from inadvertently escaping the interior of inner tube (234) proximally.

As gap (251) of channel (254) receives liquid coolant, the liquid coolant contacts blade (260) to thereby provide a cooling effect to blade (260) (e.g., through quenching, etc.). Thus, from the discussion above, it should be understood that pivoting of trigger (228) toward and away from pistol grip (224) will pump liquid coolant from fluid reservoir (270) to sleeve (250) via fluid pump (280). In some versions, each actuation of trigger (228) delivers approximately 280 microliters of liquid coolant to sleeve (250). Alternatively, any other suitable volume of liquid coolant may be delivered to sleeve (250) with each actuation of trigger (220).

While the proximal end of sleeve (250) is disposed within inner tube (234) of the present example, sleeve (250) may be modified such that the proximal end of sleeve (250) is disposed about the exterior of outer sheath (232). In such examples, sleeve (250) may still provide clearance for inner tube (234) to translate longitudinally without interference from sleeve (250). Such modified versions of sleeve may also still provide a fluid seal relative to outer sheath (232), thereby directing liquid coolant from interior space (233) to gap (251) to thereby cool blade (260). As yet another merely illustrative example, sleeve (250) may be replaced with any of the liquid cooling features described in U.S. patent application Ser. No. 14/552,530, entitled "Features to Apply Fluid to an Ultrasonic Blade of a Surgical Instrument," filed on Nov. 25, 2014, issued as U.S. Pat. No. 10,034,685 on Jul. 31, 2018, the disclosure of which is incorporated by reference herein. Still other variations will be apparent to those of ordinary skill in the art in view of the teachings herein.

IV. Exemplary Ultrasonic End Effector with Dual Use Ports

Figure 30:
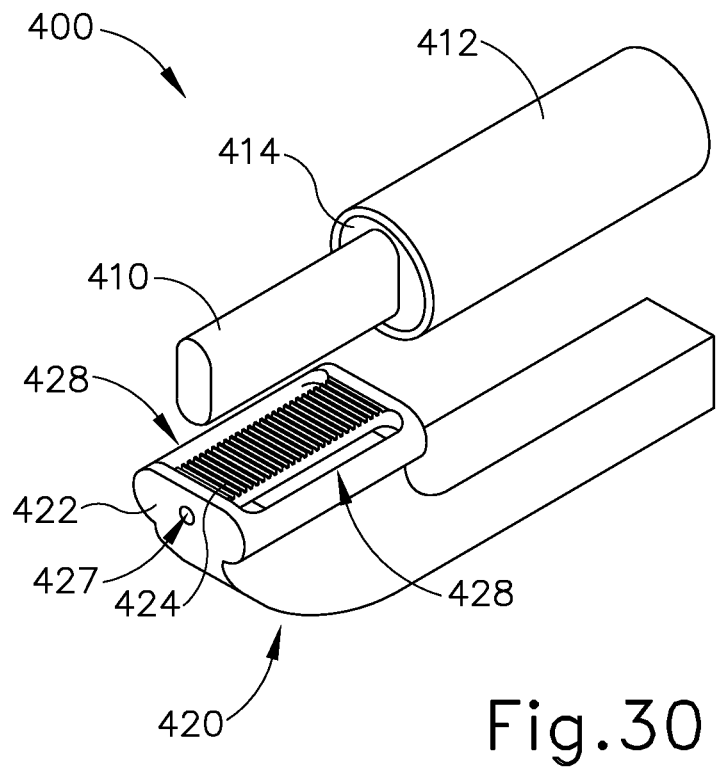
FIG. 30 depicts a perspective view of an exemplary alternative end effector for an ultrasonic surgical instrument.
Figure 31:
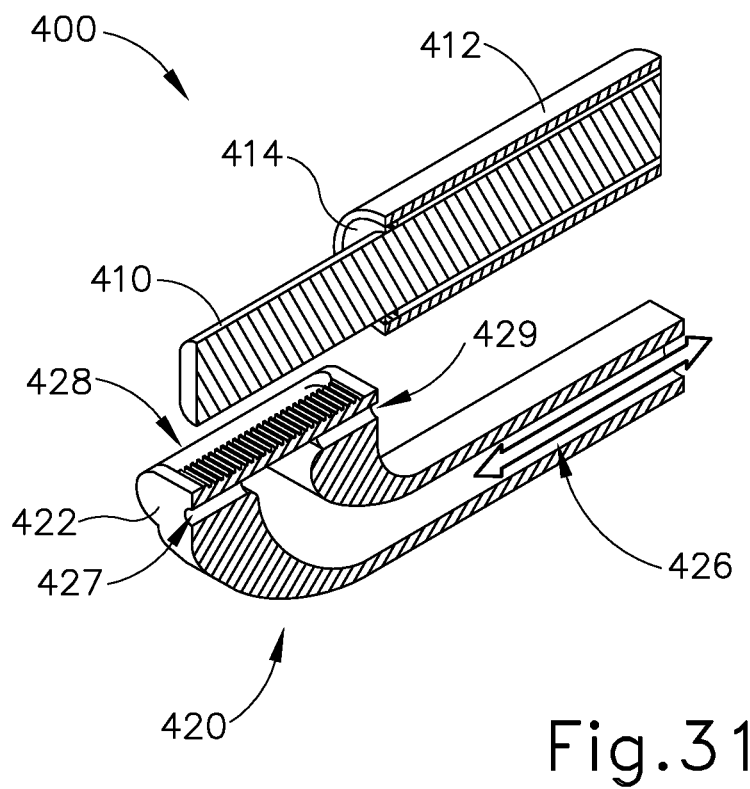
FIG. 31 depicts a cross-sectional view of the end effector of FIG. 30.
Figure 32:
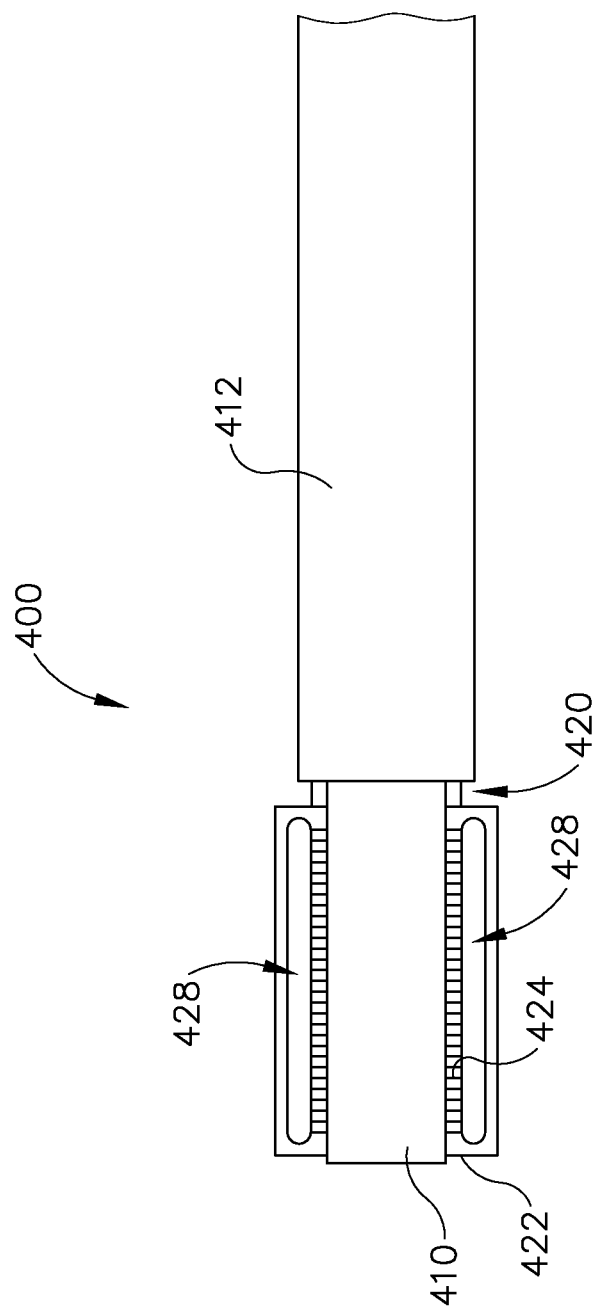
FIG. 32 depicts a top plan view of the end effector of FIG. 30.

FIGS. 30-32 show an exemplary alternative end effector (400) that is operable to communicate with a source of liquid coolant. It should be understood that end effector (400) may be incorporated into any instrument (10, 100, 200) described herein and/or any instrument described in any reference that is cited herein. End effector (400) of this example comprises an ultrasonic blade (410) and a clamp arm (420) that is movable toward and away from ultrasonic blade (410) to compress tissue against ultrasonic blade (420). Ultrasonic blade (410) may be selectively activated to vibrate at ultrasonic frequencies in accordance with the teachings herein and/or in accordance with the teachings of any reference that is cited herein. Similarly, clamp arm (420) may be actuated to move toward and away from ultrasonic blade (410) in accordance with the teachings herein and/or in accordance with the teachings of any reference that is cited herein.

An outer sheath (412) is disposed about ultrasonic blade (410). A seal (414) is interposed between ultrasonic blade (410) and the distal end of outer sheath (412). Seal (414) is located at a longitudinal position corresponding to a node associated with resonant ultrasonic vibrations communicated through ultrasonic blade (410). Seal (414) is configured to prevent fluids from entering outer sheath (412); and to provide structural support for the distal end of outer sheath (412). It should be understood that one or more additional seals (414) may be provided on one or more respective nodal locations of a waveguide that is coupled with ultrasonic blade (410), along at least part of the length of outer sheath (412), to provide further support to outer sheath (412). It should also be understood that at least a distal-most seal (414) may be omitted in some versions to provide an a pathway for fluid communication of liquid coolant, suction, etc., as described herein, between the exterior of blade (410) and the interior of outer sheath (412).

Clamp arm (420) of the present example comprises a clamp pad (422) having a tissue contacting surface (424). In the present example, tissue contacting surface (424) has a plurality of transversely extending ridges that are configured to enhance the grip of tissue as clamp pad (422) compresses the tissue against ultrasonic blade (410), though it should be understood that tissue contacting surface (424) may include any other suitable kind(s) of surface features or geometry. As shown in FIG. 31, clamp arm (420) defines a lumen (426). The distal end of lumen (426) is in fluid communication with a set of openings (427, 428, 429). Opening (427) is formed at the distal end of clamp arm (420), under tissue contacting surface (424) of clamp pad (422). Elongate openings (428) are formed along the lateral sides of tissue contacting surface (424). As best seen in FIG. 32, clamp arm (420) is configured such that elongate openings (428) are spaced apart by a width that is greater than the width of ultrasonic blade (410). In some other versions, the width of separation between elongate openings (428) is reduced, such that the width is equal to or less than width of ultrasonic blade (410). Opening (429) is formed at the proximal end of clamp arm (420), under tissue contacting surface (424) of clamp pad (422). In some alternative versions, opening (427) is omitted. In some other alternative versions, openings (428) are omitted. In some other alternative versions, opening (429) is omitted. In still other versions, openings (428, 429) are omitted, such that opening (427) is the only opening. Other suitable variations will be apparent to those of ordinary skill in the art in view of the teachings herein.

The proximal end of lumen (426) may be placed in fluid communication with a fluid source in any suitable fashion. By way of example only, lumen (426) may be in fluid communication with fluid pump (280) via knob assembly (300). Other suitable ways in which lumen (426) may be placed in fluid communication with a fluid source will be apparent to those of ordinary skill in the art in view of the teachings herein. It should also be understood that lumen (426) may be used for various kinds of fluid communication in addition to or as an alternative to communicating liquid coolant. By way of example only, lumen (426) may be used to communicate suction through openings (427, 428, 429), to administer medical fluid (e.g., analgesic, therapeutic, etc.) through openings (427, 428, 429), and/or to provide any other kind of fluid communication. In versions where lumen (426) is used to provide suction through openings (427, 428, 429), such suction may be used to draw spatter, fumes, smoke, bodily fluids, excess liquid coolant, irrigation fluid, etc. from the surgical site when end effector (400) is being used to manipulate tissue at the surgical site. In versions where lumen (426) is used to provide a liquid such as saline through openings (427, 428, 429), such liquid may cool blade (410) and/or irrigate the surgical site (e.g., flushing debris from the surgical site to improve access to target tissue and/or visibility of target tissue). Furthermore, lumen (426) may be selectively coupled with more than one fluid source, such that an operator may selectively switch between different kinds of fluid sources within a given medical procedure. Other suitable ways in which fluid communication may be provided through lumen (426) will be apparent to those of ordinary skill in the art in view of the teachings herein.

By way of example only, end effector (400) may be used to perform a tonsillectomy in a patient. For instance, end effector (400) may be positioned at the base of the patient's tonsil while end effector (400) is in an open configuration. The operator may then close end effector (400) about the base of the tonsil by driving clamp arm (420) toward ultrasonic blade (410). With the base of the tonsil being compressed against blade (410) by clamp pad (422), the operator may then ultrasonically activate blade (410). The combination of compression against blade (410) and ultrasonic activation of blade (410) may simultaneously sever and seal the tissue at the base of the tonsil, thereby separating the tonsil from the underlying tissue bed and allowing the tonsil to be pulled from the patient's mouth using conventional forceps. While blade (410) is being activated and/or at any other appropriate time, liquid coolant may be communicated through openings (427, 428, 429) to reduce the heat of blade (410) and/or to prevent blade (410) from getting excessively hot. By communicating liquid coolant through openings (427, 428, 429), the cooling of blade (410) may prevent blade (410) from otherwise causing inadvertent thermal trauma to the delicate tonsil bed. In addition or in the alternative, openings (427, 428, 429) may be used to provide suction, medical fluid, and/or any other suitable kind of fluid communication at the tonsil removal site. Of course, end effector (400) may be used in various other ways and in various other kinds of medical procedures. The present example of a tonsillectomy is being provided merely for illustrative purposes only.

V. Miscellaneous

In some exemplary versions, the same vibrational movement that is used to drive an ultrasonic blade (24, 160) during tissue cutting/sealing may drive liquid distally along blade (24, 160). As yet another merely illustrative example, fluid may be communicated to and/or along blade (24, 160) in accordance with at least some of the teachings of U.S. Pub. No. 2011/0152759, entitled "Use of Biomarkers and Therapeutic Agents with Surgical Devices," published Jun. 23, 2011, issued as U.S. Pat. No. 8,591,459 on Nov. 26, 2013, the disclosure of which is incorporated by reference herein. It should be understood that the teachings in U.S. Pub. No. 2011/0152759, issued as U.S. Pat. No. 8,591,459 on Nov. 26, 2013, relating to dispensation of medical fluids may be readily adapted to provide communication of cooling fluid. It should also be understood that the teachings herein may be readily combined with the teachings of U.S. patent application Ser. No. 14/553,329, entitled "Features to Drive Fluid toward an Ultrasonic Blade of a Surgical Instrument," filed on Nov. 25, 2014, issued as U.S. Pat. No. 10,004,529 on Jun. 26, 2018, the disclosure of which is incorporated by reference herein; U.S. patent application Ser. No. 14/553,378, entitled "Ultrasonic Surgical Instrument with Blade Cooling through Retraction," filed on Nov. 25, 2014, published as U.S. Pub. No. 2016/0143659 on May 26, 2016, the disclosure of which is incorporated by reference herein; and U.S. patent application Ser. No. 14/552,530, entitled "Features to Apply Fluid to an Ultrasonic Blade of a Surgical Instrument," filed on Nov. 25, 2014, issued as U.S. Pat. No. 10,034,685 on Jul. 31, 2018, the disclosure of which is incorporated by reference herein.

In addition to or as an alternative to using fluid to reduce heat in a version of instrument (10, 100), one or more shielding features may be used to avoid direct contact between a hot portion of instrument (10, 100) and tissue (or other structures). A gap may be defined between the shielding feature and the corresponding hot portion of instrument (10, 100), to avoid or minimize communication of heat from the hot portion of instrument (10, 100) and the shielding feature. Such a gap may be filled with liquid, air or some other gas, a solid insulating material, and/or any other suitable kind of filler, including combinations thereof. It should also be understood that various kinds of structural features may be interposed between the hot portion of instrument (10, 100) and the shielding feature, including but not limited to a roughened surface, grooves, dimples, pimples, nubs, knurling, a honeycomb structure, etc. Such structural features may minimize transfer of heat from the hot portion of instrument (10, 100) and the shielding feature. Similarly, a shielding feature (and/or a hot feature of instrument (10, 100)) may include external surface structures such as a roughened surface, grooves, dimples, pimples, nubs, knurling, a honeycomb structure, etc., to minimize transfer of heat from the shielding feature (or hot feature) to adjacent tissue, etc. Various merely illustrative examples of shielding features are described in U.S. Provisional Patent App. No. 61/908,920, the disclosure of which is incorporated by reference herein; and also in U.S. patent application Ser. No. 14/552,552, entitled "Shielding Features for Ultrasonic Blade of a Surgical Instrument," filed on Nov. 25, 2014, issued as U.S. Pat. No. 9,993,260 on May 12, 2018, the disclosure of which is incorporated by reference herein; and also in U.S. patent application Ser. No. 14/552,681, entitled "Sleeve Features for Ultrasonic Blade of a Surgical Instrument," filed on Nov. 25, 2014, issued as U.S. Pat. No. 10,004,528 on Jun. 26, 2018, the disclosure of which is incorporated by reference herein. It should be understood that the teachings herein may be readily combined with the teachings of those references and the various other references cited herein. Other suitable examples will be apparent to those of ordinary skill in the art in view of the teachings herein.

In some instances, the heating at an end effector (40, 140) may be caused or hastened by direct contact between clamp pad (46, 146) and blade (42, 142) while clamp arm (44, 144) is closed and blade (42, 142) is activated, etc. Such direct contact may occur at regions where tissue is not interposed between clamp pad (46, 146) and blade (42, 142). Some operators may position tissue just between the distal portion of clamp pad (46, 146) and the distal portion of blade (42, 142). This may occur when end effector (40, 140) is used to transect relatively small vessels. When this occurs, the distal portions of clamp pad (46, 146) and blade (42, 142) may both contact the tissue compressed between clamp pad (46, 146) and blade (42, 142); yet the proximal portions of clamp pad (46, 146) and blade (42, 142) may just directly contact each other. When blade (42, 142) is activated in such instances, clamp pad (46, 146) and blade (42, 142) may rapidly generate a significant amount of heat at the proximal portions where the direct contact occurs.

It may therefore be desirable to minimize the amount of direct contact between clamp pad (46, 146) and blade (42, 142), particularly at the proximal regions of clamp pad (46, 146) and blade (42, 142). In other words, it may be desirable to provide staged engagement between clamp pad (46, 146) and blade (42, 142), such that the distal regions of clamp pad (46, 146) and blade (42, 142) engage first; then the proximal regions of clamp pad (46, 146) and blade (42, 142). Various examples of how an end effector (40, 140) may provide such staged engagement are described in U.S. Provisional Patent App. No. 61/908,920, the disclosure of which is incorporated by reference herein; and also in U.S. patent application Ser. No. 14/552,614, entitled "Ultrasonic Surgical Instrument with Staged Clamping," filed on Nov. 25, 2014, issued as U.S. Pat. No. 10,004,527 on Jul. 26, 2018, the disclosure of which is incorporated by reference herein. It should be understood that the teachings herein may be readily combined with the teachings of those references and the various other references cited herein. Other examples will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a body;
   (b) a shaft assembly distally extending from the body and including a shaft fluid passageway configured to communicate a fluid therethrough;
   (c) an end effector distally extending from the shaft assembly, including:
      (i) an ultrasonic blade, and
      (ii) an end passageway in fluid communication with the shaft fluid passageway and configured to discharge the fluid toward the ultrasonic blade;
   (d) a fluid pump fluidly connected to the shaft fluid passageway and configured to connect to a fluid source, wherein the fluid pump includes:

(i) an interior, and
(ii) a piston received within the interior and configured to selectively move through a vacuum stroke and a pressure stroke, wherein selectively moving the piston through the vacuum stroke is configured to generate the vacuum within the interior of the fluid pump, and wherein selectively moving the piston through the pressure stroke is configured to generate the pressure within the interior of the fluid pump;
(e) a pumping input operatively connected to the fluid pump and configured to selectively move between a first position and a second position,
wherein selectively directing the pumping input from the first position toward the second position is configured to generate a vacuum in the fluid pump for drawing the fluid from the fluid source and into the fluid pump, and
wherein selectively directing the pumping input from the second position toward the first position is configured to generate a pressure in the fluid pump for forcing the fluid from the fluid pump toward the shaft fluid passageway and discharging the fluid from the end passageway thereby cooling the ultrasonic blade,
wherein the pumping input is operatively connected to the piston such that selectively directing the pumping input from the first position toward the second position thereby moves the piston through the vacuum stroke and selectively directing the pumping input from the second position toward the first position thereby moves the piston through the pressure stroke.

2. The surgical instrument of claim 1, wherein the fluid pump is contained within the body and the pumping input is supported by the body.

3. The surgical instrument of claim 1, wherein the fluid pump further includes:
(i) a pump inlet configured to connect to a fluid source,
(ii) a pump outlet fluidly connected to the shaft fluid passageway, and
(iii) the interior in fluid communication between the pump inlet and the pump outlet.

4. The surgical instrument of claim 1, further comprising a trigger movably connected to the body and configured to be selectively manipulated by an operator, and wherein the trigger is operatively connected to the pumping input such that selective manipulation of the trigger selectively directs movement of the pumping input.

5. The surgical instrument of claim 4, wherein the end effector further includes a clamp arm configured to move relative to the ultrasonic blade between an open position and a closed position, wherein the ultrasonic blade and the clamp arm in the open position are configured to receive a tissue therebetween, wherein the ultrasonic blade and the clamp arm in the closed position are configured to compress a tissue therebetween, and wherein the trigger is also operatively connected to the clamp arm.

6. The surgical instrument of claim 5, wherein the trigger is configured to simultaneously move the pumping input and the clamp arm.

7. The surgical instrument of claim 6, wherein the trigger is further configured to simultaneously move the pumping input to the first position and the clamp arm to the open position.

8. The surgical instrument of claim 7, further comprising a yoke operatively connected between the trigger, the pumping input, and the clamp arm.

9. The surgical instrument of claim 8, wherein the pumping input is a plunger extending from the yoke toward the fluid pump.

10. The surgical instrument of claim 6, wherein the trigger is further configured to simultaneously move the pumping input to the second position and the clamp arm to the closed position.

11. The surgical instrument of claim 1, wherein the end effector further includes a clamp arm configured to move relative to the ultrasonic blade between an open position and a closed position, wherein the ultrasonic blade and the clamp arm in the open position are configured to receive a tissue therebetween, wherein the ultrasonic blade and the clamp arm in the closed position are configured to compress a tissue therebetween, and wherein the clamp arm is configured to simultaneously move with the pumping input.

12. The surgical instrument of claim 11, wherein the clamp arm is in the open position when the pumping input is in the first position.

13. The surgical instrument of claim 11, wherein the clamp arm is in the closed position when the pumping input is in the second position.

14. The surgical instrument of claim 11, further comprising a yoke operatively connected between the pumping input and the clamp arm.

15. The surgical instrument of claim 14, wherein the pumping input is a plunger extending from the yoke toward the fluid pump.

16. A surgical instrument, comprising:
(a) a body;
(b) a shaft assembly distally extending from the body and including a shaft fluid passageway configured to communicate a fluid therethrough;
(c) an end effector distally extending from the shaft assembly, including:
(i) an ultrasonic blade,
(ii) a clamp arm configured to move relative to the ultrasonic blade between an open position and a closed position, wherein the ultrasonic blade and the clamp arm in the open position are configured to receive a tissue therebetween, wherein the ultrasonic blade and the clamp arm in the closed position are configured to compress a tissue therebetween, and
(iii) an end passageway in fluid communication with the shaft fluid passageway and configured to discharge the fluid toward the ultrasonic blade;
(d) a fluid pump contained within the body, including:
(i) a pump inlet configured to connect to a fluid source,
(ii) a pump outlet fluidly connected to the shaft fluid passageway,
(iii) an interior in fluid communication between the pump inlet and the pump outlet, and
(iv) a piston received within the interior and configured to selectively move through a vacuum stroke and a pressure stroke, wherein selectively moving the piston through the vacuum stroke is configured to generate a vacuum within the interior of the fluid pump, and wherein selectively moving the piston through the pressure stroke is configured to generate a pressure within the interior of the fluid pump,
(e) a pumping input supported by the body, operatively connected to the piston, and configured to selectively move between a first position and a second position,
(f) a trigger movably connected to the body and configured to be selectively manipulated by an operator, and wherein the trigger is operatively connected to the pumping input and the clamp arm such that selective manipulation of the trigger selectively directs movement of the pumping input and the clamp arm, wherein selectively directing the pumping input from the first position toward the second position via the trigger is configured to move the piston through the vacuum stroke for drawing the fluid from the fluid source and into the interior of the fluid pump, and wherein selectively directing the pumping input from the second position toward the first position via the trigger is configured to move the piston through the pressure stroke for forcing the fluid from the fluid pump toward the shaft fluid passageway and discharging the fluid from the end passageway thereby cooling the ultrasonic blade.

17. The surgical instrument of claim 16, wherein the trigger is configured to simultaneously move the pumping input and the clamp arm.

18. The surgical instrument of claim 17, further comprising a yoke operatively connected between the trigger, the pumping input, and the clamp arm.

19. The surgical instrument of claim 18, further comprising a fluid source including a fluid reservoir, and wherein the fluid source is supported by the body and fluidly connected to the pump inlet.

20. A surgical instrument, comprising:
(a) a body;
(b) a shaft assembly distally extending from the body and including a shaft fluid passageway configured to communicate a fluid therethrough;
(c) an end effector distally extending from the shaft assembly, including:
  (i) an ultrasonic blade,
  (ii) an end passageway in fluid communication with the shaft fluid passageway and configured to discharge the fluid toward the ultrasonic blade, and
  (iii) a clamp arm configured to move relative to the ultrasonic blade between an open position and a closed position, wherein the ultrasonic blade and the clamp arm in the open position are configured to receive a tissue therebetween, wherein the ultrasonic blade and the clamp arm in the closed position are configured to compress a tissue therebetween;
(d) a fluid pump fluidly connected to the shaft fluid passageway and configured to connect to a fluid source; and
(e) a pumping input operatively connected to the fluid pump and configured to selectively move between a first position and a second position, wherein selectively directing the pumping input from the first position toward the second position is configured to generate a vacuum in the fluid pump for drawing the fluid from the fluid source and into the fluid pump, wherein selectively directing the pumping input from the second position toward the first position is configured to generate a pressure in the fluid pump for forcing the fluid from the fluid pump toward the shaft fluid passageway and discharging the fluid from the end passageway thereby cooling the ultrasonic blade, and wherein the clamp arm is configured to simultaneously move with the pumping input such that the clamp arm is in the open position when the pumping input is in the first position or such that the clamp arm is in the closed position when the pumping input is in the second position.

* * * * *